United States Patent
Kelliher et al.

(10) Patent No.: US 10,179,759 B2
(45) Date of Patent: Jan. 15, 2019

(54) MULTI-STEP SEPARATION PROCESS

(71) Applicant: BASF Pharma (Callanish) Limited, Cheshire (GB)

(72) Inventors: Adam Kelliher, Cheshire (GB); Angus Morrison, Cheshire (GB)

(73) Assignee: BASF Pharma (Callanish) Limited, Cheadle, Cheshire (GB)

( * ) Notice: Subject to any disclaimer, the term of this patent is extended or adjusted under 35 U.S.C. 154(b) by 0 days.

(21) Appl. No.: 15/411,690

(22) Filed: Jan. 20, 2017

(65) Prior Publication Data

US 2017/0129845 A1    May 11, 2017

Related U.S. Application Data

(63) Continuation of application No. 14/759,764, filed as application No. PCT/GB2014/050054 on Jan. 9, 2014, now Pat. No. 9,694,302.

(Continued)

(30) Foreign Application Priority Data

Jan. 9, 2013  (GB) .................................. 1300354.6

(51) Int. Cl.
   *C07C 57/03*    (2006.01)
   *C07C 69/587*   (2006.01)
   (Continued)

(52) U.S. Cl.
   CPC ............... *C07C 57/03* (2013.01); *A23D 9/04* (2013.01); *B01D 15/185* (2013.01);
   (Continued)

(58) Field of Classification Search
   CPC ........... C11C 1/08; B01D 15/08; B01D 15/22; B01D 15/36; B01D 15/185;
   (Continued)

(56) References Cited

U.S. PATENT DOCUMENTS 2,985,589 A   5/1961   Broughton et al.
3,696,107 A   10/1972  Neuzil
(Continued)

FOREIGN PATENT DOCUMENTS

DK   1338316   3/2005
DK   1128881   10/2005
(Continued)

OTHER PUBLICATIONS

Mjos, S. A., The prediction of fatty acid structgure from selected ions in electron impact mass spectra of fatty acid methyl esters, 2004, Eur. J. Lipid Sci. Technol., vol. 106, pp. 550-560 (Year: 2004).*

(Continued)

*Primary Examiner* — Yate' K Cutliff
(74) *Attorney, Agent, or Firm* — Knobbe Martens Olson & Bear LLP

(57) ABSTRACT

The present invention provides a chromatographic separation process for recovering a polyunsaturated fatty acid (PUFA) product from a feed mixture, which comprises: (a) purifying the feed mixture in a first chromatographic separation step using an eluent a mixture of water and a first organic solvent, to obtain an intermediate product; and (b) purifying the intermediate product in a second chromatographic separation step using as eluent a mixture of water and a second organic solvent, to obtain the PUFA product, wherein the second organic solvent is different from the first organic solvent and has a polarity index which differs from the polarity index of the first organic solvent by between 0.1 and 2.0, wherein the PUFA product is other than alpha-linolenic acid (ALA), gamma-linolenic acid (GLA), linoleic acid, an ALA mono- di- or triglyceride, a GLA mono- di- or triglyceride, a linoleic acid mono- di- or triglyceride, an ALA $C_1$-$C_4$ alkyl ester, a GLA $C_1$-$C_4$ alkyl ester or a linoleic acid $C_1$-$C_4$ alkyl ester or a mixture thereof.

11 Claims, 16 Drawing Sheets

Related U.S. Application Data

(60) Provisional application No. 61/750,389, filed on Jan. 9, 2013.

(51) Int. Cl.
*B01D 15/18* (2006.01)
*A23D 9/04* (2006.01)
*C11B 3/10* (2006.01)
*C11C 1/08* (2006.01)
*B01D 15/42* (2006.01)

(52) U.S. Cl.
CPC ....... *B01D 15/1892* (2013.01); *B01D 15/426* (2013.01); *C07C 69/587* (2013.01); *C11B 3/10* (2013.01); *C11C 1/08* (2013.01)

(58) Field of Classification Search
CPC .... B01D 15/1821; B01D 15/426; A23D 9/04; C07C 57/03; C07C 69/587
See application file for complete search history.

(56) References Cited

U.S. PATENT DOCUMENTS

| | | | |
|---|---|---|---|
| 3,706,812 A | 12/1972 | Derosset et al. | |
| 3,761,533 A | 9/1973 | Otani et al. | |
| 4,036,745 A | 7/1977 | Broughton | |
| 4,048,111 A | 9/1977 | Rosback et al. | |
| 4,048,205 A | 9/1977 | Neuzil et al. | |
| 4,049,688 A | 9/1977 | Neuzil et al. | |
| 4,313,015 A | 1/1982 | Broughton | |
| 4,329,280 A | 5/1982 | Cleary et al. | |
| 4,353,838 A | 10/1982 | Cleary et al. | |
| 4,353,839 A | 10/1982 | Cleary et al. | |
| 4,404,145 A | 9/1983 | Cleary et al. | |
| 4,433,195 A | 2/1984 | Kulprathipanja | |
| 4,486,618 A | 12/1984 | Kulprathipanja et al. | |
| 4,495,106 A | 1/1985 | Cleary et al. | |
| 4,511,514 A | 4/1985 | Cleary et al. | |
| 4,519,952 A | 5/1985 | Cleary et al. | |
| 4,521,343 A | 6/1985 | Chao et al. | |
| 4,522,761 A | 6/1985 | Cleary et al. | |
| 4,524,029 A | 6/1985 | Cleary et al. | |
| 4,524,030 A | 6/1985 | Cleary et al. | |
| 4,524,049 A | 6/1985 | Sit | |
| 4,529,551 A | 7/1985 | Cleary et al. | |
| 4,560,675 A | 12/1985 | Cleary et al. | |
| 4,605,783 A | 8/1986 | Zinnen | |
| 4,720,579 A | 1/1988 | Kulprathipanja | |
| 4,764,276 A | 8/1988 | Berry et al. | |
| 4,882,065 A | 11/1989 | Barder | |
| 4,902,829 A | 2/1990 | Kulprathipanja et al. | |
| 4,961,881 A | 10/1990 | Ou | |
| 5,068,418 A | 11/1991 | Kulprathipanja et al. | |
| 5,068,419 A | 11/1991 | Kulprathipanja et al. | |
| 5,069,883 A | 12/1991 | Matonte | |
| 5,093,004 A | 3/1992 | Hotier | |
| 5,114,590 A | 5/1992 | Hotier et al. | |
| 5,179,219 A | 1/1993 | Priegnitz | |
| 5,189,189 A * | 2/1993 | Misawa ................ | C07C 51/487 554/194 |
| 5,225,580 A | 7/1993 | Zinnen | |
| 5,405,534 A | 4/1995 | Ishida et al. | |
| 5,422,007 A | 6/1995 | Nicoud et al. | |
| 5,502,077 A | 3/1996 | Breivik et al. | |
| 5,547,580 A | 8/1996 | Tsujii et al. | |
| 5,656,667 A | 8/1997 | Breivik et al. | |
| 5,698,594 A | 12/1997 | Breivik et al. | |
| 5,719,302 A * | 2/1998 | Perrut ...................... | C11B 3/16 554/191 |
| 5,777,141 A | 7/1998 | Brunner et al. | |
| 5,840,181 A | 11/1998 | Patton et al. | |
| 5,917,068 A | 6/1999 | Barnicki et al. | |
| 5,945,318 A | 8/1999 | Breivik et al. | |
| 6,013,186 A | 1/2000 | Patton et al. | |
| 6,063,284 A | 5/2000 | Grill | |
| 6,096,218 A | 8/2000 | Hauck | |
| 6,136,198 A | 10/2000 | Adam et al. | |
| 6,204,401 B1 | 3/2001 | Perrut et al. | |
| 6,313,330 B1 | 11/2001 | Kiyohara et al. | |
| 6,325,898 B1 | 12/2001 | Blehaut et al. | |
| 6,350,890 B1 | 2/2002 | Kiy et al. | |
| 6,409,923 B1 | 6/2002 | Nicoud et al. | |
| 6,413,419 B1 | 7/2002 | Adam et al. | |
| 6,471,870 B1 | 10/2002 | Nicoud | |
| 6,518,049 B1 | 2/2003 | Haraldsson et al. | |
| 6,544,413 B1 | 4/2003 | Nagamatsu et al. | |
| 6,713,447 B2 | 3/2004 | Beaudoin et al. | |
| 6,789,502 B2 | 9/2004 | Hjaltason et al. | |
| 6,863,824 B2 | 3/2005 | Hamende et al. | |
| 6,979,402 B1 | 12/2005 | Sprague et al. | |
| 7,063,855 B2 | 6/2006 | Hialtason et al. | |
| 7,462,643 B1 | 12/2008 | Pamparana | |
| 7,491,522 B2 | 2/2009 | Haraldsson et al. | |
| 7,541,480 B2 | 6/2009 | Bruzzese | |
| 7,588,791 B2 | 9/2009 | Fabritius | |
| 7,667,061 B2 | 2/2010 | Binder et al. | |
| 7,678,930 B2 | 3/2010 | Sondbo et al. | |
| 7,705,170 B2 | 4/2010 | Geier et al. | |
| 7,709,236 B2 | 5/2010 | Akimoto et al. | |
| 7,718,698 B2 | 5/2010 | Breivik et al. | |
| 7,732,488 B2 | 6/2010 | Breivik et al. | |
| 7,807,848 B2 | 10/2010 | Wang | |
| 8,063,235 B2 | 11/2011 | Krumbholz et al. | |
| 8,216,475 B2 | 7/2012 | Valery et al. | |
| 8,282,831 B2 | 10/2012 | Kessler et al. | |
| 2002/0011445 A1 | 1/2002 | Lehoucq et al. | |
| 2002/0068833 A1 | 6/2002 | Chanteloup et al. | |
| 2003/0006191 A1 | 1/2003 | Heikkila et al. | |
| 2003/0216543 A1 | 11/2003 | Wanq et al. | |
| 2003/0222024 A1 | 12/2003 | Hamende et al. | |
| 2004/0099604 A1 | 5/2004 | Hauck | |
| 2004/0174769 A1 | 9/2004 | Weetman | |
| 2005/0087494 A1 | 4/2005 | Hauck et al. | |
| 2006/0008667 A1 | 1/2006 | Kim et al. | |
| 2006/0124549 A1 | 6/2006 | Bailly et al. | |
| 2007/0068873 A1 | 3/2007 | Oroskar et al. | |
| 2007/0148315 A1 | 6/2007 | Schaap et al. | |
| 2007/0158270 A1 | 7/2007 | Geier et al. | |
| 2007/0181504 A1 | 8/2007 | Binder et al. | |
| 2008/0234375 A1 | 9/2008 | Breivik et al. | |
| 2009/0023808 A1 | 1/2009 | Raman et al. | |
| 2009/0176284 A1 | 7/2009 | Furihata et al. | |
| 2010/0012584 A1 | 1/2010 | Majewski et al. | |
| 2010/0069492 A1 | 3/2010 | Geiringer et al. | |
| 2010/0104657 A1 | 4/2010 | Sondbo et al. | |
| 2010/0160435 A1 | 6/2010 | Bruzzese | |
| 2010/0163490 A1 | 7/2010 | Lasalle | |
| 2010/0176058 A1 | 7/2010 | Brytesson | |
| 2010/0186587 A1 | 7/2010 | Kessler et al. | |
| 2010/0190220 A1 | 7/2010 | Furihata et al. | |
| 2010/0197785 A1 | 8/2010 | Breivik et al. | |
| 2010/0233281 A1 | 9/2010 | Breivik et al. | |
| 2010/0267829 A1 | 10/2010 | Breivik et al. | |
| 2010/0278879 A1 | 11/2010 | Manku | |
| 2010/0331559 A1 | 12/2010 | Feist et al. | |
| 2010/0331561 A1 | 12/2010 | Schaap et al. | |
| 2011/0000853 A1 | 1/2011 | Valery et al. | |
| 2011/0015418 A1 | 1/2011 | Krumbholz et al. | |
| 2011/0030457 A1 | 2/2011 | Valery et al. | |
| 2011/0091947 A1 | 4/2011 | Kim et al. | |
| 2011/0139001 A1 | 6/2011 | Hiliareau et al. | |
| 2011/0168632 A1 | 7/2011 | Valery et al. | |
| 2012/0214966 A1 | 8/2012 | Theoleyre et al. | |
| 2012/0225120 A1* | 9/2012 | Manku ................ | A61K 9/4858 424/456 |
| 2012/0232141 A1 | 9/2012 | Hustvedt et al. | |

FOREIGN PATENT DOCUMENTS

| | | |
|---|---|---|
| EP | 0255824 | 7/1987 |
| EP | A-0610506 | 5/1993 |
| EP | 0697034 | 11/1994 |
| EP | 0981399 | 11/1998 |

(56) References Cited

FOREIGN PATENT DOCUMENTS

| | | | | |
|---|---|---|---|---|
| EP | 1152755 | 8/2000 | | |
| EP | 1 065 196 | 1/2001 | | |
| EP | 1065196 | * 1/2001 | ............ | C07C 51/47 |
| EP | 1106602 | 6/2001 | | |
| EP | 1250058 | 7/2001 | | |
| EP | 1250059 | 7/2001 | | |
| EP | 1157692 | 11/2001 | | |
| EP | 1 211 304 A2 | 6/2002 | | |
| EP | 1392411 | 11/2002 | | |
| EP | 1436370 | 4/2003 | | |
| EP | 1523541 | 1/2004 | | |
| EP | 1534807 | 1/2004 | | |
| EP | 1685222 | 6/2005 | | |
| EP | 1749079 | 10/2005 | | |
| EP | 1982752 | 10/2008 | | |
| EP | 2173184 | 1/2009 | | |
| EP | 2173699 | 1/2009 | | |
| EP | 2169038 | 3/2010 | | |
| EP | 2295529 | 7/2012 | | |
| FR | 2103302 | 7/1971 | | |
| FR | 2651148 | 3/1991 | | |
| FR | 2651149 | 3/1991 | | |
| FR | 2897238 | 8/2007 | | |
| GB | 2221843 | 2/1990 | | |
| HK | 1078509 | 6/2006 | | |
| JP | 58-088339 | 5/1983 | | |
| JP | 58-109444 | 6/1983 | | |
| JP | S58109444 A | 6/1983 | | |
| JP | 60-208940 | 10/1985 | | |
| JP | 61-192797 | 8/1986 | | |
| JP | S6388159 | 4/1988 | | |
| JP | H01-197596 A | 8/1989 | | |
| JP | H03-167294 | 7/1991 | | |
| JP | H04-235701 | 8/1992 | | |
| JP | H05-222392 | 8/1993 | | |
| JP | 6287594 | 10/1994 | | |
| JP | 6287594 A | 10/1994 | | |
| JP | H07-242895 | 9/1995 | | |
| JP | H08-100191 | 4/1996 | | |
| JP | 09-157684 | 6/1997 | | |
| JP | H09-151390 | 6/1997 | | |
| JP | H09-310089 | 12/1997 | | |
| JP | H10-7618 | 1/1998 | | |
| JP | H10-310555 | 11/1998 | | |
| JP | H10310556 A | 11/1998 | | |
| JP | 11-057302 | 3/1999 | | |
| JP | 2872986 B | 3/1999 | | |
| JP | 2872986 B1 | 3/1999 | | |
| JP | H11-80083 A | 3/1999 | | |
| JP | 11-090105 | 4/1999 | | |
| JP | 2000-270885 | 10/2000 | | |
| JP | 2000280663 | 10/2000 | | |
| JP | 2001-72993 | 3/2001 | | |
| JP | 2001139981 | 5/2001 | | |
| JP | 2003-530572 | 10/2003 | | |
| JP | WO 2004/018072 | 3/2004 | | |
| JP | 2005-534495 | 11/2005 | | |
| JP | 2006-133160 | 5/2006 | | |
| JP | 3905538 | 1/2007 | | |
| JP | 2008-061571 | 3/2008 | | |
| JP | 4170542 B2 | 8/2008 | | |
| JP | 2009-529890 | 8/2009 | | |
| JP | 2009-529891 | 8/2009 | | |
| JP | 2010-183881 A | 8/2010 | | |
| KR | 2002-0082718 | 4/2001 | | |
| SI | 1797021 | 4/2009 | | |
| WO | WO 87/03899 | 7/1987 | | |
| WO | WO 91/01965 | 2/1991 | | |
| WO | WO 94/25552 | 11/1994 | | |
| WO | WO 98/32514 | 7/1998 | | |
| WO | WO 1998/051656 | 11/1998 | | |
| WO | WO 9947228 | 9/1999 | | |
| WO | WO 00/25885 | 5/2000 | | |
| WO | WO 01/077662 | 10/2001 | | |
| WO | WO 01/87451 | 11/2001 | | |
| WO | WO 01/87452 | 11/2001 | | |
| WO | WO 01/87924 | 11/2001 | | |
| WO | WO 2004/007654 | 1/2004 | | |
| WO | WO 2005/100519 | 10/2005 | | |
| WO | WO 2007/012750 | 2/2007 | | |
| WO | WO 2007/017240 | 2/2007 | | |
| WO | WO 2007/038417 | 4/2007 | | |
| WO | WO 2007/075499 | 7/2007 | | |
| WO | WO 2007/093690 | 8/2007 | | |
| WO | WO 2007/147554 | 12/2007 | | |
| WO | WO 2008/004900 | 1/2008 | | |
| WO | WO 2008/054228 | 5/2008 | | |
| WO | WO 2008/107562 | 9/2008 | | |
| WO | WO 2008/149177 | 12/2008 | | |
| WO | WO 2009/047408 | 4/2009 | | |
| WO | WO 2009/105351 | 8/2009 | | |
| WO | WO 2010/018423 | 2/2010 | | |
| WO | WO 2010/119319 | 10/2010 | | |
| WO | WO 2011/048169 | 4/2011 | | |
| WO | WO 2011/080503 | * 7/2011 | ............ | B01D 15/18 |
| WO | WO 2013/005046 | 1/2013 | | |
| WO | WO 2013/005047 | 1/2013 | | |
| WO | WO 2013/005048 | 1/2013 | | |
| WO | WO 2013/005051 | 1/2013 | | |
| WO | WO 2013/005052 | 1/2013 | | |
| ZA | 8905758 | 4/1990 | | |

OTHER PUBLICATIONS

Operation and Utilizing manner of a Liquid Chromatography Device (Mar. 11, 2008, retrieved at URL: http://www.wakayama-edc.big-u.jp/kankyo/ekikuro/ekikuro.pdf).

Third Party Submission of Information submitted on Mar. 3, 2017 in Japanese Application No. 2015-10829.

Reference Table 1 Chlorinated dioxins in health food using fish oil toxicity equivalent and intake, retrieved at http://www.mhlw.go.jp/topics/bukyoku/iyaku/syoku-anzen/dioxin/sessyu05/d1/03-03i.pdf (Jul. 30, 2008).

Survey results on the survey of daily intake of dioxins from food in FY 2007, retrieved at http://www.mhlw.go.jp/topics/bukyoku/iyaku/syoku-anzen/dioxin/sessyu07/index.html(Jul. 30, 2008).

Survey results on the survey of daily intake of dioxins from foods in FY 2008, retrieved at http://www.mhlw.go.jp/topics/bukyoku/iyaku/syoku-anzen/dioxin/sessyu08/index.html (Sep. 30, 2009).

Survey results on the survey on daily intake of dioxins from foods in FY 2009, retrieved at http://www.mhlw.go.jp/topics/bukyoku/iyaku/syoku-anzen/dioxin/sessyu09/index.html (Oct. 8, 2010).

"International Search Report in PCT/GB2010/002339", dated Jul. 7, 2011, 7 pages.

"International Search Report in PCT/GB2014/050054", dated May 23, 2014, 5 pages.

"International Search Report and Written Opinion of PCT/GB2012/051591", dated Sep. 27, 2012, 13 pages.

"International Search Report and Written Opinion of PCT/GB2012/051592", dated Sep. 27, 2012, 10 pages.

"International Search Report and Written Opinion of PCT/GB2012/051593", dated Sep. 27, 2012, 10 page.

"International Search Report and Written Opinion of PCT/GB2012/051596", dated Sep. 27, 2012, 13 pages.

"International Search Report and Written Opinion of PCT/GB2012/051597", dated Sep. 27, 2012, 13 pages.

"Written Opinion of the ISA in PCT/GB2010/002339", dated Jun. 30, 2012, 10 pages.

"Written Opinion of the ISA in PCT/GB2014/050054", dated Jul. 9, 2015, 6 pages.

Guiochon, Georges et al., "Fundamentals of Preparative and Non-linear Chromatography", Elsevier 2006, 833-835.

Heinisch, Sabine et al., "Sense and nonsense of high-temperature liquid chromatography", Journal of Chromatography A 1216 2009, 642-658.

Non-Final Office Action in U.S. Appl. No. 13/519,618, dated Jan. 23, 2015, 5pages.

Non-Final Office Action in U.S. Appl. No. 13/880,145, dated Jun. 24, 2015, 15 pages.

(56) References Cited

OTHER PUBLICATIONS

Non-Final Office Action in U.S. Appl. No. 13/880,146, dated Jul. 9, 2015, 6 pages.
Non-Final Office Action in U.S. Appl. No. 13/880,148, dated Feb. 20, 2015, 5 pages.
Non-Final Office Action in U.S. Appl. No. 13/880,150, dated Oct. 9, 2015, 20 pages.
Non-Final Office Action in U.S. Appl. No. 13/880,154, dated Apr. 1, 2015, 6 pages.
Non-Final Office Action in U.S. Appl. No. 14/759,764, dated Dec. 31, 2015, 21 pages.
Non-Final Office Action in U.S. Appl. No. 14/870,873, dated Jan. 20, 2016, 14 pages.
Quan, Wenqin, "Study on the enrichment of glyceride of .omega.-3PUFA", Chinese Master's Theses Full-text Database Basic Sciences, A0062-42 Mar. 15, 2009.
Quan, Wenqin et al., "Determination of eicosapentaenoic acid and docosahexaenoic acid in fish oil by high performance liquid chromatography/mass spectrometry", Food & Machinery, vol. 24, No. 2, pp. 114-117 (English translation without bibliography) Mar. 31, 2008, 4 pages.
Santos, M.A.G. et al., "Simulated Moving-Bed Adsorption for Separation of Racemic Mixtures", Brazilian Journal of Chemical Engineering, vol. 21, No. 01 2004, 127-136.
Szepesy, et al., "Journal of Chromatography", vol. 108, No. 2, 1975, pp. 285-297.
Xie, et al., "Biotechnology Progress", American Institute of Chemical Engineers vol. 18, No. 6 2002, 1332-1344.
Tao, et al., Study on extracting high contents of DHA and EPA by using silver nitrate-water method. Chinese Journal of Marine Drugs, (2004) 99:28-30.
Communication pursuant to Rule 114(2) EPC dated Dec. 1, 2016 in European Patent Application No. 12735933.9, Patent No. EP 2613859.
Snyder et al., "Preparative Separations"—Introduction to Modern Liquid Chromatography, Chapter 15, Third Edition, 2010, Wiley & Sons, Inc.
Snyder et al., "Basic Concepts and the Control of Separation"—Introduction to Modern Liquid Chromatography, Chapter 2, Third Edition, 2010, Wiley & Sons, Inc.
Third party submission of information submitted on Jan. 31, 2017 in Japanese Application No. 2014-517954.
Office Action dated Sep. 12, 2017 in Japanese Application No. 215346/2016, filed Sep. 5, 2017.
Office Action dated Oct. 11, 2017 in Korean Application No. 10-2017-7021341, filed on Jul. 28, 2017.
Non-Final Office Action in U.S. Appl. No. 15/411,702, dated Oct. 3, 2017.
The third party observations filed on Jan. 25, 2018 relating to EP 13154052.8.
The Home of Fine Lipid Organics, Nu-Chek Prep, Inc. Catalog, Mar. 18, 2009.

\* cited by examiner

FIRST SMB SEPARATION STEP         SECOND SMB SEPARATION STEP

→ FLOW OF ELUENT          → FLOW OF ELUENT

← FLOW OF ADSORBENT       ← FLOW OF ADSORBENT

MULTI-STEP SEPARATION PROCESS

CROSS-REFERENCE TO RELATED APPLICATIONS

This application is a continuation application of U.S. patent application Ser. No. 14/759,764, filed Jul. 8, 2015, which is the National Phase entry of International Application No. PCT/GB2014/050054, filed Jan. 9, 2014, which claims priority of Great Britain Patent Application No. 1300354.6, filed Jan. 9, 2013, and claims the benefit of U.S. Provisional Patent Application No. 61/750,389, filed Jan. 9, 2013. The contents of these related applications are incorporated by reference herein in their entireties.

DESCRIPTION

The present invention relates to an improved chromatographic separation process for purifying polyunsaturated fatty acids (PUFAs) and derivatives thereof. In particular, the present invention relates to an improved chromatographic separation process which employs a mixed solvent system.

BACKGROUND OF THE INVENTION

Fatty acids, in particular PUFAs, and their derivatives are precursors for biologically important molecules, which play an important role in the regulation of biological functions such as platelet aggregation, inflammation and immunological responses. Thus, PUFAs and their derivatives may be therapeutically useful in treating a wide range of pathological conditions including CNS conditions; neuropathies, including diabetic neuropathy; cardiovascular diseases; general immune system and inflammatory conditions, including inflammatory skin diseases.

PUFAs are found in natural raw materials, such as vegetable oils and marine oils. Such PUFAs are, however, frequently present in such oils in admixture with saturated fatty acids and numerous other impurities. PUFAs should therefore desirably be purified before nutritional or pharmaceutical uses.

Unfortunately, PUFAs are extremely fragile. Thus, when heated in the presence of oxygen, they are prone to isomerization, peroxidation and oligomerization. The fractionation and purification of PUFA products to prepare pure fatty acids is therefore difficult. Distillation, even under vacuum, can lead to non-acceptable product degradation.

Chromatographic separation techniques are well known to those of skill in the art. Chromatographic separation techniques involving stationary bed systems and simulated or actual moving bed systems are both familiar to one of skill in the art.

In a conventional stationary bed chromatographic system, a mixture whose components are to be separated percolates through a container. The container is generally cylindrical, and is typically referred to as the column. The column contains a packing of a porous material (generally called the stationary phase) exhibiting a high permeability to fluids. The percolation velocity of each component of the mixture depends on the physical properties of that component so that the components exit from the column successively and selectively. Thus, some of the components tend to fix strongly to the stationary phase and thus will percolate slowly, whereas others tend to fix weakly and exit from the column more quickly. Many different stationary bed chromatographic systems have been proposed and are used for both analytical and industrial production purposes.

Simulated and actual moving bed chromatography are known techniques, familiar to those of skill in the art. The principle of operation involves countercurrent movement of a liquid eluent phase and a solid adsorbent phase. This operation allows minimal usage of solvent making the process economically viable. Such separation technology has found several applications in diverse areas, including hydrocarbons, industrial chemicals, oils, sugars and APIs.

Thus, a simulated moving bed chromatography apparatus consists of a number of individual columns containing adsorbent which are connected together in series. Eluent is passed through the columns in a first direction. The injection points of the feedstock and the eluent, and the separated component collection points in the system, are periodically shifted by means of a series of valves. The overall effect is to simulate the operation of a single column containing a moving bed of the solid adsorbent, the solid adsorbent moving in a countercurrent direction to the flow of eluent. Thus, a simulated moving bed system consists of columns which, as in a conventional stationary bed system, contain stationary beds of solid adsorbent through which eluent is passed, but in a simulated moving bed system the operation is such as to simulate a continuous countercurrent moving bed.

A typical simulated moving bed chromatography apparatus is illustrated with reference to FIG. 1. The concept of a simulated or actual moving bed chromatographic separation process is explained by considering a vertical chromatographic column containing stationary phase S divided into sections, more precisely into four superimposed sub-zones I, II, III and IV going from the bottom to the top of the column. The eluent is introduced at the bottom at IE by means of a pump P. The mixture of the components A and B which are to be separated is introduced at IA+B between sub-zone II and sub-zone III. An extract containing mainly B is collected at SB between sub-zone I and sub-zone II, and a raffinate containing mainly A is collected at SA between sub-zone III and sub-zone IV.

In the case of a simulated moving bed system, a simulated downward movement of the stationary phase S is caused by movement of the introduction and collection points relative to the solid phase. In the case of an actual moving bed system, simulated downward movement of the stationary phase S is caused by movement of the various chromatographic columns relative to the introduction and collection points. In FIG. 1, eluent flows upward and mixture A+B is injected between sub-zone II and sub-zone III. The components will move according to their chromatographic interactions with the stationary phase, for example adsorption on a porous medium. The component B that exhibits stronger affinity to the stationary phase (the slower running component) will be more slowly entrained by the eluent and will follow it with delay. The component A that exhibits the weaker affinity to the stationary phase (the faster running component) will be easily entrained by the eluent. If the right set of parameters, especially the flow rate in each sub-zone, are correctly estimated and controlled, the component A exhibiting the weaker affinity to the stationary phase will be collected between sub-zone III and sub-zone IV as a raffinate and the component B exhibiting the stronger affinity to the stationary phase will be collected between sub-zone I and sub-zone II as an extract.

It will therefore be appreciated that the conventional simulated moving bed system schematically illustrated in FIG. 1 is limited to binary fractionation.

Processes and equipment for simulated moving bed chromatography are described in several patents, including U.S. Pat. Nos. 2,985,589, 3,696,107, 3,706,812, 3,761,533, FR-A-2103302, FR-A-2651148 and FR-A-2651149, the entirety of which are incorporated herein by reference. The topic is also dealt with at length in "Preparative and Production Scale Chromatography", edited by Ganetsos and Barker, Marcel Dekker Inc, New York, 1993, the entirety of which is incorporated herein by reference.

An actual moving bed system is similar in operation to a simulated moving bed system. However, rather than shifting the injection points of the feed mixture and the eluent, and the separated component collection points by means of a system of valves, instead a series of adsorption units (i.e. columns) are physically moved relative to the feed and drawoff points. Again, operation is such as to simulate a continuous countercurrent moving bed.

Processes and equipment for actual moving bed chromatography are described in several patents, including U.S. Pat. Nos. 6,979,402, 5,069,883 and 4,764,276, the entirety of which are incorporated herein by reference.

Purification of PUFA products is particularly challenging. Thus, many suitable feedstocks for preparing PUFA products are extremely complex mixtures containing a large number of different components with very similar retention times in chromatography apparatuses. It is therefore very difficult to separate certain PUFAs from such feedstocks. However, a high degree of purity of PUFA products is required, particularly for pharmaceutical and nutraceutical applications. Historically, therefore, distillation has been used when high purity PUFA products are required. There are, however, significant drawbacks to using distillation as a separation technique for delicate PUFAs as discussed above.

Published international patent application WO-A-2011/080503, the entirety of which is incorporated herein by reference, discloses an SMB separation process for recovering a PUFA product from a feed mixture efficiently and in very high purity. It has been found, however, that it can be difficult to remove C18 fatty acids, in particular alpha-linolenic acid (ALA) and/or gamma-linolenic acid (GLA), from feed mixtures efficiently without using large volumes of aqueous alcohol solvents. Efficient removal of C18 fatty acids is advantageous since many specifications for pharmaceutical and dietary oils require a low content of these fatty acids. For example, certain oil specifications for use in Japan require an ALA content of less than 1 wt %.

Accordingly, there is a need for a chromatographic separation process which can efficiently recover a PUFA product from a feed mixture whilst minimising the amount of C18 fatty acids, for example ALA and/or GLA, present in the resultant product.

SUMMARY OF THE INVENTION

It has now been surprisingly found that a PUFA product with low levels of C18 fatty acids, for example ALA and/or GLA, can be effectively purified from commercially available feedstocks such as fish oils by using a mixed solvent system.

The present invention therefore provides a chromatographic separation process for recovering a polyunsaturated fatty acid (PUFA) product from a feed mixture, which comprises:

(a) purifying the feed mixture in a first chromatographic separation step using as eluent a mixture of water and a first organic solvent, to obtain an intermediate product; and (b) purifying the intermediate product in a second chromatographic separation step using as eluent a mixture of water and a second organic solvent, to obtain the PUFA product, wherein the second organic solvent is different from the first organic solvent and has a polarity index which differs from the polarity index of the first organic solvent by between 0.1 and 2.0, wherein the PUFA product is not alpha-linolenic acid (ALA), gamma-linolenic acid (GLA), linoleic acid, an ALA mono- di- or triglyceride, a GLA mono- di- or triglyceride, a linoleic acid mono, di- or triglyceride, an ALA $C_1$-$C_4$ alkyl ester, a GLA $C_1$-$C_4$ alkyl ester or a linoleic acid $C_1$-$C_4$ alkyl ester or a mixture thereof.

Also provided is a PUFA product obtainable by the process of the present invention.

Also provided is a composition comprising a PUFA product obtainable by the process of the present invention.

DETAILED DESCRIPTION OF THE INVENTION

Figure 1:
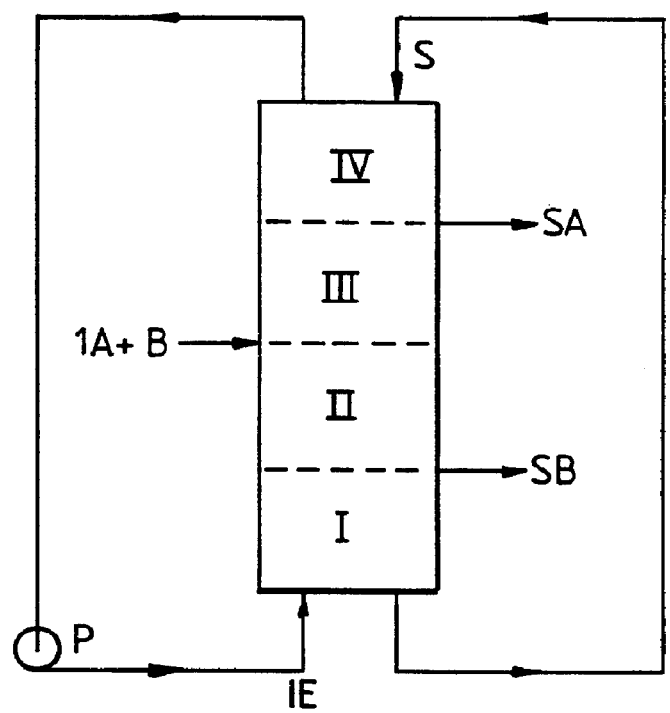
FIG. 1 illustrates the basic principles of a simulated or actual moving bed process for separating a binary mixture.

In its most general sense, the present invention provides a chromatographic separation process for recovering a polyunsaturated fatty acid (PUFA) product from a feed mixture, which comprises:
(a) purifying the feed mixture in a first chromatographic separation step using as eluent a mixture of water and a first organic solvent, to obtain an intermediate product; and
(b) purifying the intermediate product in a second chromatographic separation step using as eluent a mixture of water and a second organic solvent, to obtain the PUFA product, wherein the second organic solvent is different from the first organic solvent and has a polarity index which differs from the polarity index of the first organic solvent by between 0.1 and 2.0.

As used herein, the term "PUFA product" refers to a product comprising one or more polyunsaturated fatty acids (PUFAs), and/or derivatives thereof, typically of nutritional or pharmaceutical significance. Typically, the PUFA product is a single PUFA or derivative thereof. Alternatively, the PUFA product is a mixture of two or more PUFAs or derivatives thereof.

The term "polyunsaturated fatty acid" (PUFA) refers to fatty acids that contain more than one double bond. Such PUFAs are well known to the person skilled in the art. As used herein, a PUFA derivative is a PUFA in the form of a mono-, di- or tri-glyceride, ester, phospholipid, amide, lactone, or salt. Mono-, di- and triglycerides and esters are preferred. Triglycerides and esters are more preferred. Esters are even more preferred. Esters are typically alkyl esters, preferably $C_1$-$C_6$ alkyl esters, more preferably $C_1$-$C_4$ alkyl esters. Examples of esters include methyl and ethyl esters. Ethyl esters are most preferred.

Typically, the PUFA product is at least one ω-3 or ω-6 PUFA or a derivative thereof, preferably at least one ω-3 PUFA or a derivative thereof.

Examples of ω-3 PUFAs include eicosatrienoic acid (ETE), eicosatetraenoic acid (ETA), eicosapentaenoic acid (EPA), docosapentaenoic acid (DPA) and docosahexaenoic acid (DHA). EPA, DPA and DHA are preferred. EPA and DHA are most preferred.

Examples of ω-6 PUFAs include eicosadienoic acid, dihomo-gamma-linolenic acid (DGLA), arachidonic acid (ARA), docosadienoic acid, adrenic acid and docosapentaenoic (ω-6) acid. ARA and DGLA are preferred.

Preferably, the PUFA product is EPA, DHA, a derivative thereof or mixtures thereof. Typical derivatives include EPA and DHA mono-, di- and triglycerides and EPA and DHA esters, preferably alkyl esters such as $C_1$-$C_4$ alkyl esters.

More preferably, the PUFA product is EPA, DHA, or a derivative thereof. Typical derivatives include EPA and DHA mono-, di- and triglycerides and EPA and DHA esters, preferably alkyl esters such as $C_1$-$C_4$ alkyl esters.

Most preferably, the PUFA product is eicosapentaenoic acid (EPA), docosahexaenoic acid (DHA), EPA triglycerides, DHA triglycerides, EPA ethyl ester or DHA ethyl ester.

Particularly preferably, the PUFA product is EPA, DHA, EPA ethyl ester or DHA ethyl ester.

In one embodiment, the PUFA product is EPA and/or EPA ethyl ester (EE)

In another embodiment, the PUFA product is DHA and/or DHA ethyl ester (EE).

In a yet further embodiment, the PUFA product is a mixture of EPA and DHA and/or EPA EE and DHA EE.

In a most preferred embodiment, the PUFA product obtained in the second separation step is EPA or an EPA derivative, for example EPA ethyl ester, and is obtained at a purity greater than 90 wt %, preferably greater than 95 wt %, more preferably greater than 97 wt %, even more preferably greater than 98 wt %, still more preferably greater than 98.4 wt %. Preferably, the PUFA product obtained in the second separation step is EPA or an EPA derivative, for example EPA ethyl ester, and is obtained at a purity between 98 and 99.5 wt %.

Typically, in addition to said PUFA product, an additional secondary PUFA product is collected in the chromatographic separation process of the invention. Preferably, the PUFA product is EPA or a derivative thereof and the additional secondary PUFA product is DHA or a derivative thereof.

In a further embodiment of the invention, the process is configured to collect a PUFA product which is a concentrated mixture of EPA and DHA or derivatives thereof. Thus, a feed mixture is used which contains EPA, DHA, components which are more polar than EPA and DHA, and components which are less polar than EPA and DHA.

Typically, the PUFA product contains less than 1 wt % of alpha-linolenic acid (ALA), ALA mono-, di- and triglyceride and ALA $C_1$-$C_4$ alkyl ester impurities. More typically, the PUFA product contains less than 1 wt % of impurities which are ALA and derivatives thereof. Typical ALA derivatives are as defined above for PUFA derivatives.

Typically, the PUFA product contains less than 1 wt % of gamma-linolenic acid (GLA), GLA mono-, di- and triglyceride and GLA $C_1$-$C_4$ alkyl ester impurities. More typically, the PUFA product contains less than 1 wt % of impurities which are GLA and derivatives thereof. Typical GLA derivatives are as defined above for PUFA derivatives.

Typically, the PUFA product contains less than 1 wt % of C18 fatty acid impurities, C18 fatty acid mono-, di- and triglyceride impurities and C18 fatty acid alkyl ester impurities. More typically, the PUFA product contains less than 1 wt % of impurities which are C18 fatty acids and derivatives thereof. Typical C18 fatty acid derivatives are as defined above for PUFA derivatives. As used herein, a C18 fatty acid is a C18 aliphatic monocarboxylic acid having a straight or branched hydrocarbon chain. Typical C18 fatty acids include stearic acid (C18:0), oleic acid (C18:1n9), vaccenic acid (C18:1n7), linoleic acid (C18:2n6), gamma-linolenic acid/GLA (C18:3n6), alpha-linolenic acid/ALA (C18:3n3) and stearidonic acid/SDA (C18:4n3).

For the avoidance of doubt, in these embodiments the maximum amount of all of the specified impurities is 1 wt %.

As explained above, typically the amount of the above-mentioned impurities in the PUFA product is less than 1 wt %. Preferably, the amount of the above-mentioned impurities is less than 0.5 wt %, more preferably less than 0.25 wt %, even more preferably less than 0.1 wt %, yet more preferably less than 0.05 wt %, yet more preferably less than 0.01 wt %, yet more preferably less than 0.001wt %, yet more preferably less than 0.0001 wt %, yet more preferably less than 0.00001 wt %.

In certain preferred embodiments, the PUFA product is substantially free of the above-mentioned impurities.

The PUFA product is not ALA, GLA, linoleic acid, an ALA mono- di- or triglyceride, a GLA mono- di- or triglyceride, a linoleic acid mono, di- or triglyceride, an ALA $C_1$-$C_4$ alkyl ester, a GLA $C_1$-$C_4$ alkyl ester or a linoleic acid $C_1$-$C_4$ alkyl ester or a mixture thereof. Typically, the PUFA product is not ALA, GLA, linoleic acid, or a derivative or mixtures thereof. Typical ALA, GLA and linoleic acid derivatives are as defined above for PUFA derivatives.

Typically, the PUFA product is not a C18 PUFA, a C18 PUFA mono-, di-or triglyceride, or a C18 PUFA alkyl ester. Thus, the present invention provides a chromatographic separation process for recovering a polyunsaturated fatty acid (PUFA) product from a feed mixture, which comprises:
  (a) purifying the feed mixture in a first chromatographic separation step using as eluent a mixture of water and a first organic solvent, to obtain an intermediate product; and
  (b) purifying the intermediate product in a second chromatographic separation step using as eluent a mixture of water and a second organic solvent, to obtain the PUFA product, wherein the second organic solvent is different from the first organic solvent and has a polarity index which differs from the polarity index of the first organic solvent by between 0.1 and 2.0,
wherein the PUFA product is other than a C18 PUFA, a C18 PUFA mono-, di- or triglyceride, or a C18 PUFA alkyl ester.

More typically, the PUFA product is not a C18 PUFA or a C18 PUFA derivative. Typical C18 PUFAs include linoleic acid (C18:2n6), GLA (C18:3n6), and ALA (C18:3n3).

Suitable feed mixtures for separating by the process of the present invention may be obtained from natural sources including vegetable and animal oils and fats, and from synthetic sources including oils obtained from genetically modified plants, animals and micro organisms including yeasts. Examples include fish oils, algal and microalgal oils and plant oils, for example borage oil, Echium oil and evening primrose oil. In one embodiment, the feed mixture is a fish oil. In another embodiment, the feed mixture is an algal oil. Algal oils are particularly suitable when the desired PUFA product is EPA and/or DHA. Genetically modified yeast is particularly suitable when the desired PUFA product is EPA.

In a particularly preferred embodiment the feed mixture is a fish oil or fish-oil derived feedstock. It has advantageously been found that when a fish-oil or fish-oil derived feed stock is used, an EPA or EPA ethyl ester PUFA product can be produced by the process of the present invention in greater than 90% purity, preferably greater than 95% purity, more preferably greater than 97% purity, even more preferably greater than 98 wt %, still more preferably greater than 98.4 wt %, for example between 98 and 99.5 wt %.

The feed mixture may undergo chemical treatment before fractionation by the process of the invention. For example, it may undergo glyceride transesterification or glyceride hydrolysis followed in certain cases by selective processes such as crystallisation, molecular distillation, urea fractionation, extraction with silver nitrate or other metal salt solutions, iodolactonisation or supercritical fluid fractionation. Alternatively, a feed mixture may be used directly with no initial treatment step.

The feed mixtures typically contain the PUFA product and at least one more polar component and at least one less polar component. The less polar components have a stronger adherence to the adsorbent used in the process of the present invention than does the PUFA product. During operation, such less polar components typically move with the solid adsorbent phase in preference to the liquid eluent phase. The more polar components have a weaker adherence to the adsorbent used in the process of the present invention than does the PUFA product. During operation, such more polar components typically move with the liquid eluent phase in preference to the solid adsorbent phase. In general, more polar components will be separated into a raffinate stream, and less polar components will be separated into an extract stream.

The feed mixture typically contains the PUFA product and at least one C18 fatty acid impurity as defined above. Thus, more typically the feed mixture contains the PUFA product and at least one C18 fatty acid and/or derivative thereof. Typical C18 fatty acid derivatives are as defined above for PUFA derivatives. Preferably, the feed mixture contains the PUFA product and at least one C18 fatty acid impurity chosen from stearic acid (C18:0), oleic acid (C18:1n9), vaccenic acid (C18:1n7), linoleic acid (C18:2n6), gamma-linolenic acid/GLA (C18:3n6), alpha-linolenic acid (C18:3n3) and stearidonic acid/SDA (C18:4n3) and derivatives thereof.

Preferably, the feed mixture comprises (i) the PUFA product, and/or a mono-, di- or triglyceride of the PUFA product and/or a $C_1$-$C_4$ alkyl ester of the PUFA product, and (ii) ALA and/or a mono-, di- or triglyceride of ALA and/or a $C_1$-$C_4$ alkyl ester of ALA.

Preferably, the feed mixture comprises (i) the PUFA product, and/or a mono-, di- or triglyceride of the PUFA product and/or a $C_1$-$C_4$ alkyl ester of the PUFA product, and (ii) GLA and/or a mono-, di- or triglyceride of GLA and/or a $C_1$-$C_4$ alkyl ester of GLA.

More preferably, the feed mixture comprises (i) the PUFA product, and/or a mono-, di- or triglyceride of the PUFA product and/or a $C_1$-$C_4$ alkyl ester of the PUFA product, and (ii) ALA and/or GLA and/or a mono-, di- or triglyceride of ALA and/or a mono-, di- or triglyceride of GLA and/or a $C_1$-$C_4$ alkyl ester of ALA and/or a $C_1$-$C_4$ alkyl ester of GLA.

In embodiments where the PUFA product contains less than 1 wt % of the above-specified C18 fatty acid impurities, the feed mixture typically contains the specified C18 fatty acid impurities. Thus, it is a particular advantage of the present invention that the amount of C18 fatty acid impurities present in a feed mixture can be reduced to a low level by the process of the present invention. For example, where the PUFA product contains less than 1 wt % of ALA, ALA mono-, di- and triglycerides and ALA $C_1$-$C_4$ alkyl esters, the feed mixture typically contains ALA, ALA mono-, di- and triglycerides and/or ALA $C_1$-$C_4$ alkyl esters. Where the PUFA product contains less than 1 wt % of GLA, GLA mono-, di- and triglycerides and GLA $C_1$-$C_4$ alkyl esters, the feed mixture typically contains GLA, GLA mono-, di- and triglycerides and/or GLA $C_1$-$C_4$ alkyl esters. Where the PUFA product contains less than 1 wt % of C18 fatty acids, C18 fatty acid mono-, di- and triglycerides and C18 fatty acid alkyl esters, the feed mixture typically contains C18 fatty acids, C18 fatty acid mono-, di- and triglycerides and/or C18 fatty acid alkyl esters.

Examples of the more and less polar components include (1) other compounds occurring in natural oils (e.g. marine oils or vegetable oils), (2) byproducts formed during storage, refining and previous concentration steps and (3) contaminants from solvents or reagents which are utilized during previous concentration or purification steps.

Examples of (1) include other unwanted PUFAs; saturated fatty acids; sterols, for example cholesterol; vitamins; and environmental pollutants, such as polychlorobiphenyl (PCB), polyaromatic hydrocarbon (PAH) pesticides, chlorinated pesticides, dioxines and heavy metals. PCB, PAH, dioxines and chlorinated pesticides are all highly non-polar components.

Examples of (2) include isomers and oxidation or decomposition products from the PUFA product, for instance, auto-oxidation polymeric products of fatty acids or their derivatives.

Examples of (3) include urea which may be added to remove saturated or mono-unsaturated fatty acids from the feed mixture.

Preferably, the feed mixture is a PUFA-containing marine oil (e.g. a fish oil), more preferably a marine oil (e.g. a fish oil) comprising EPA and/or DHA.

A typical feed mixture for preparing concentrated EPA (EE) by the process of the present invention comprises 50-75% EPA (EE), 0 to 10% DHA (EE), and other components including other essential ω-3 and ω-6 fatty acids.

A preferred feed mixture for preparing concentrated EPA (EE) by the process of the present invention comprises 55% EPA (EE), 5% DHA (EE), and other components including other essential ω-3 and ω-6 fatty acids. DHA (EE) is less polar than EPA(EE).

A typical feed mixture for preparing concentrated DHA (EE) by the process of the present invention comprises 50-75% DHA (EE), 0 to 10% EPA (EE), and other components including other essential ω-3 and ω-6 fatty acids.

A preferred feed mixture for preparing concentrated DHA (EE) by the process of the present invention comprises 75% DHA (EE), 7% EPA (EE) and other components including other essential ω-3 and ω-6 fatty acids. EPA (EE) is more polar than DHA (EE).

A typical feed mixture for preparing a concentrated mixture of EPA (EE) and DHA (EE) by the process of the present invention comprises greater than 33% EPA (EE), and greater than 22% DHA (EE).

The process of the present invention involves at least two chromatographic separation steps, where a mixture of water and a different organic solvent is used as eluent in each step. The first and second separation steps are carried out using mixtures of water and first and second organic solvents respectively.

Typically, neither eluent is in a supercritical state. Typically, both eluents are liquids.

The first and second organic solvents are typically chosen from alcohols, ethers, esters, ketones and nitriles. Alcohols and nitriles are preferred.

Alcohol solvents are well known to the person skilled in the art. Alcohols are typically short chain alcohols. Alcohols typically are of formula ROH, wherein R is a straight or branched C1-C6 alkyl group. The C1-C6 alkyl group is preferably unsubstituted. Examples of alcohols include methanol, ethanol, n-propanol, i-propanol, n-butanol, i-butanol, s-butanol and t-butanol. Methanol and ethanol are preferred. Methanol is more preferred.

Ether solvents are well known to the person skilled in the art. Ethers are typically short chain ethers. Ethers typically are of formula R—O—R', wherein R and R' are the same or different and represent a straight or branched C1-C6 alkyl group. The C1-C6 alkyl group is preferably unsubstituted. Preferred ethers include diethylether, diisopropylether, and methyl t-butyl ether (MTBE).

Ester solvents are well known to the person skilled in the art. Esters are typically short chain esters. Esters typically are of formula R—(C=O)O—R', wherein R and R' are the same or different and represent a straight or branched C1-C6 alkyl group. Preferred esters include methylacetate and ethylacetate.

Ketone solvents are well known to the person skilled in the art. Ketones are typically short chain ketones. Ketones typically are of formula R—(C=O)—R', wherein R and R' are the same or different and represent a straight or branched C1-C6 alkyl group. The C1-C6 alkyl group is preferably unsubstituted. Preferred ketones include acetone, methylethylketone and methyl isobutyl ketone (MIBK).

Nitrile solvents are well known to the person skilled in the art. Nitriles are typically short chain nitriles. Nitriles typically are of formula R—CN, wherein R represents a straight or branched C1-C6 alkyl group. The C1-C6 alkyl group is preferably unsubstituted. Preferred nitriles include acetonitrile.

The second organic solvent is different from the first organic solvent.

The polarity index (P') of a solvent is a well-known measure of how polar a solvent is. A higher polarity index figure indicates a more polar solvent. Polarity index is typically determined by measuring the ability of a solvent to interact with various test solutes. More typically, the polarity index (P') of a solvent is as defined in Burdick and Jackson's Solvent Guide (AlliedSignal, 1997), the entirety of which is incorporated herein by reference. Burdick and Jackson rank solvents by reference to a numerical index that ranks solvents according to their different polarity. The Burdick and Jackson index is based on the structure of the solvents.

The polarity index (P') of a variety of common solvents is set out in the Table below, which is in accordance with Burdick and Jackson.

| Solvent | Polarity Index (P') |
| --- | --- |
| Pentane | 0.0 |
| 1,1,2-Trichlorotrifluoroethane | 0.0 |
| Cyclopentane | 0.1 |
| Heptane | 0.1 |
| Hexane | 0.1 |
| Iso-Octane | 0.1 |
| Petroleum Ether | 0.1 |
| Cyclohexane | 0.2 |
| n-Butyl Chloride | 1.0 |
| Toluene | 2.4 |
| Methyl t-Butyl Ether | 2.5 |
| o-Xylene | 2.5 |
| Chlorobenzene | 2.7 |
| o-Dichlorobenzene | 2.7 |
| Ethyl Ether | 2.8 |
| Dichloromethane | 3.1 |
| Ethylene Dichloride | 3.5 |
| n-Butyl Alcohol | 3.9 |
| Isopropyl Alcohol | 3.9 |
| n-Butyl Acetate | 4.0 |
| Isobutyl Alcohol | 4.0 |
| Methyl Isoamyl Ketone | 4.0 |
| n-Propyl Alcohol | 4.0 |
| Tetrahydrofuran | 4.0 |
| Chloroform | 4.1 |
| Methyl Isobutyl Ketone | 4.2 |
| Ethyl Acetate | 4.4 |
| Methyl n-Propyl Ketone | 4.5 |
| Methyl Ethyl Ketone | 4.7 |
| 1,4-Dioxane | 4.8 |
| Acetone | 5.1 |

-continued

| Solvent | Polarity Index (P') |
|---|---|
| Methanol | 5.1 |
| Ethanol | 5.2 |
| Pyridine | 5.3 |
| 2-Methoxyethanol | 5.5 |
| Acetonitrile | 5.8 |
| Propylene Carbonate | 6.1 |
| N,N-Dimethylformamide | 6.4 |
| Dimethyl Acetamide | 6.5 |
| N-Methylpyrrolidone | 6.7 |
| Dimethyl Sulfoxide | 7.2 |
| Water | 10.2 |

The second organic solvent has a polarity index which differs from the polarity index of the first organic solvent by between 0.1 and 2.0. Thus, where the polarity index of the first organic solvent is P1, the polarity index of the second organic solvent is P2, |P1-P2| is 0.1 to 2.0.

Typically, the second organic solvent has a polarity index which differs from the polarity index of the first organic solvent by at least 0.2, preferably at least 0.3, more preferably at least 0.4, still more preferably at least 0.5, and yet more preferably at least 0.6.

Typically, the second organic solvent has a polarity index which differs from the polarity index of the first organic solvent by at most 1.8, preferably at most 1.5, more preferably at most 1.3, still more preferably at most 1.0, and yet more preferably at most 0.8.

Preferably, the second organic solvent has a polarity index which differs from the polarity index of the first organic solvent by between 0.2 and 1.8, more preferably by between 0.3 and 1.5, still more preferably by between 0.4 and 1.3, yet more preferably by between 0.5 and 1.0, and most preferably by between 0.6 and 0.8.

Typically, the first and second organic solvents are miscible with water. More typically, the first and second organic solvents have a polarity index of 3.9 or greater. Preferably, the first and second organic solvents are chosen from tetrahydrofuran, isopropyl alcohol, n-propyl alcohol, methanol, ethanol, acetonitrile, 1,4-dioxane, N,N-dimethyl formamide, and dim ethyl sulphoxide.

Typically, the first organic solvent:water ratio is from 99.9:0.1 to 75:25 parts by volume, preferably from 99.5:0.5 to 80:20 parts by volume. If the first organic solvent is methanol, the methanol:water ratio is typically from 99.9:0.1 to 85:15 parts by volume, preferably from 99.5:0.5 to 88:12 parts by volume. If the first organic solvent is acetonitrile, the acetonitrile:water ratio is typically from 99:1 to 75:25 parts by volume, preferably from 96:4 to 80:20 parts by volume.

Typically, the second organic solvent:water ratio is from 99.9:0.1 to 75:25 parts by volume, preferably from 93:7 to 85:15 parts by volume. If the second organic solvent is methanol, the methanol:water ratio is typically from 95:5 to 85:15 parts by volume, preferably from 93:7 to 90:10 parts by volume. If the second organic solvent is acetonitrile, the acetonitrile:water ratio is typically from 90:10 to 80:20 parts by volume, preferably from 88:12 to 85:15 parts by volume.

Typically, one of the first and second organic solvents is acetonitrile.

Typically, one of the first and second organic solvents is methanol.

Preferably, the first and second organic solvents are selected from acetonitrile and methanol. Thus, it is preferable that (i) the first organic solvent is methanol and the second organic solvent is acetonitrile, or (ii) the first organic solvent is acetonitrile and the second organic solvent is methanol.

More preferably, the first organic solvent is methanol and the second organic solvent is acetonitrile, and (a) the methanol:water ratio is from 99.9:0.1 to 85:15 parts by volume, preferably from 99.5:0.5 to 88:12 and/or (b) the acetonitrile:water ratio is from 90:10 to 80:20 parts by volume, preferably from 88:12 to 85:15 parts by volume. In certain embodiments it is preferable that (a) the methanol:water ratio is from 91:9 to 93:7 parts by volume, and/or (b) the acetonitrile:water ratio is from 86:14 to 88:12 parts by volume.

Alternatively, the first organic solvent is acetonitrile and the second organic solvent is methanol, and (a) the acetonitrile:water ratio is from 99:1 to 75:25 parts by volume, preferably 96:4 to 80:20 parts by volume, and/or (b) the methanol:water ratio is from 95:5 to 85:15 parts by volume, preferably from 93:7 to 90:10 parts by volume. In certain embodiments it is preferable that (a) the acetonitrile:water ratio is from 86:14 to 88:12 parts by volume, and/or (b) the methanol:water ratio is from 87:13 to 89:11 parts by volume.

Each chromatographic separation step typically involves passing a feed mixture through one or more chromatographic columns. Thus, the first chromatographic separation step typically comprises passing the feed mixture through one or more chromatographic columns containing, as eluent, the mixture of water and the first organic solvent. Typically, the second chromatographic separation step comprises passing the intermediate product through one or more chromatographic columns containing, as eluent, the mixture of water and the first organic solvent. Preferably, the first chromatographic separation step comprises passing the feed mixture through one or more chromatographic columns containing, as eluent, the mixture of water and the first organic solvent, and the second chromatographic separation step comprises passing the intermediate product through one or more chromatographic columns containing, as eluent, the mixture of water and the first organic solvent. Any known chromatographic columns may be used in the claimed process.

The one or more chromatographic columns typically contains an adsorbent. Conventional adsorbents known in the art for chromatographic separation techniques may be used in the process of the present invention. When more than one chromatographic column is used, each chromatographic column may contain the same or a different adsorbent. Typically, when more than one chromatographic column is used each column contains the same adsorbent. Examples of such commonly used materials are polymeric beads, preferably polystyrene reticulated with DVB (divinylbenzene); and silica gel, preferably reverse phase bonded silica gel with C8 or C18 alkanes, especially C18. C18 bonded reverse phase silica gel is preferred. The adsorbent used in the process of the present invention is preferably non-polar.

The shape of the adsorbent stationary phase material may be, for example, spherical or nonspherical beads, preferably substantially spherical beads. Such beads typically have a diameter of 5 to 500 microns, preferably 10 to 500 microns, more preferably 15 to 500 microns, more preferably 40 to 500 microns, more preferably 100 to 500 microns, more preferably 250 to 500 microns, even more preferably 250 to 400 microns, most preferably 250 to 350 microns. In some embodiments, beads with a diameter of 5 to 35 microns may be used, typically 10 to 30 microns, preferably 15 to 25 microns. Some preferred particle sizes are somewhat larger than particle sizes of beads used in the past in simulated and actual moving bed processes. Use of larger particles enables a lower pressure of eluent to be used in the system. This, in turn, has advantages in terms of cost savings, efficiency and lifetime of the apparatus. It has surprisingly been found that adsorbent beads of large particle size may be used in the process of the present invention (with their associated advantages) without any loss in resolution.

The dimensions of the columns used are not particularly limited, and will depend to some extent on the volume of feed mixture to be purified. A skilled person would easily be able to determine appropriately sized columns to use. The diameter of each column is typically between 10 and 1000 mm, preferably between 10 and 500 mm, more preferably between 25 and 250 mm, even more preferably between 50 and 100 mm, and most preferably between 70 and 80 mm. The length of each column is typically between 10 and 300 cm, preferably between 10 and 200 cm, more preferably between 25 and 150 cm, even more preferably between 70 and 110 cm, and most preferably between 80 and 100 cm.

Any known chromatography apparatus may be used for the purposes of each separation step. The number of chromatographic columns used in each separation step is not particularly limited.

Typically, the process of the invention is carried out at room temperature, or a temperature greater than room temperature. Preferably, the process is carried out at a temperature greater than room temperature. The first and second separation steps may be carried out at the same temperature or a different temperature, preferably the same temperature.

Typically, the temperature of at least one of the chromatographic columns through which the feed mixture is passed is greater than room temperature. More typically, the temperature of all of the chromatographic columns used is greater than room temperature.

Thus, typically each chromatographic separation step involves passing a feed mixture through one or more chromatographic columns, and the temperature of at least one of those chromatographic columns is greater than room temperature. More typically, the temperature of all of the chromatographic columns used is greater than room temperature.

As will be appreciated, if at least one chromatographic column is at a temperature greater than room temperature, it is the interior of the column which is important to the separation process. Thus, it is typically the eluent and adsorbent inside the chromatographic column which may be at the temperature greater than room temperature. It is, of course, possible to achieve the required temperature inside the at least one chromatographic column by internal (for example by heating the eluent and/or feed mixture) and/or external means (for example by heating the outside of the chromatographic column by any known conventional means).

Typically, an elevated temperature can be achieved by heating the eluent and/or feed mixture. This has the effect of heating the columns internally.

Thus, the temperature of at least one of the chromatographic columns through which the feed mixture is passed can also be measured as the temperature of the eluent. Typically, therefore, the temperature of the eluent used in the first and/or second chromatographic separation steps is greater than room temperature.

Alternatively, the required temperature of at least one of the chromatographic columns may be achieved by heating the columns. The heating may be carried out using, for example, an electric heating mantle, a heated water jacket or coil or by radiative heat lamps. The interior and/or exterior of the one or more chromatographic columns may typically be heated.

The required temperature of at least one of the chromatographic columns may be achieved by heating the columns and/or the aqueous organic solvent eluent, and/or the feed mixture.

Typically, the temperature greater than room temperature is greater than 30° C., preferably greater than 35° C., more preferably greater than 40° C., even more preferably greater than 45° C., even more preferably greater than 50° C., even more preferably greater than 55° C., and even more preferably greater than 57° C. A temperature of 56° C. is useful in certain embodiments.

Typically, the temperature greater than room temperature is up to 100° C., preferably up to 95° C., more preferably up to 90° C., even more preferably up to 85° C., even more preferably up to 80° C., even more preferably up to 75° C., and even more preferably up to 70° C.

Thus, typical temperature ranges are from 30 to 100° C., from 35 to 95° C., from 40 to 90° C., from 45 to 85° C., from 50 to 80° C., from 55 to 75° C. or from 57 to 70° C.

Preferred temperature ranges are from 40 to 70° C., preferably from 50 to 67° C., more preferably from 56 to 65° C., even more preferably from 57 to 63° C.

In certain embodiments a single chromatographic column may be used, preferably a single stationary chromatographic column. Separation in this manner is typically carried out using known stationary bed chromatography apparatuses. Separation in this manner may be referred to as "stationary bed" chromatography. Typically, at least one of the first and/or second chromatographic separation steps involves at least one, for example one, "stationary bed" chromatography step.

In other embodiments, more than one chromatographic column is used. This may involve passing the feed mixture through two or more chromatographic columns, which may be the same or different, arranged in series or in parallel. The number of columns used in this embodiment is not particularly limited, but typically does not exceed thirty columns.

One particular embodiment where multiple chromatographic columns are used is simulated or actual moving bed chromatography.

Simulated and actual moving bed chromatography apparatuses are well known to the person skilled in the art. Any known simulated or actual moving bed chromatography apparatus may be utilised for the purposes of the method of the present invention, as long as the apparatus is used in accordance with the process of the present invention. Those apparatuses described in U.S. Pat. Nos. 2,985,589, 3,696,107, 3,706,812, 3,761,533, FR-A-2103302, FR-A-2651148, FR-A-2651149, U.S. Pat. Nos. 6,979,402, 5,069,883 and 4,764,276 may all be used if configured in accordance with the process of the present invention. SMB processes as disclosed in, for example, WO-A-2011/080503 may also be employed.

The first and second separation steps may be carried out using either a stationary bed chromatography apparatus, or one or more simulated or actual moving bed chromatography apparatuses as discussed herein.

Typically, the first chromatographic separation step comprises introducing the feed mixture into a stationary bed chromatography apparatus and the second chromatographic separation step comprises introducing the intermediate product into a stationary bed chromatography apparatus. Thus, typically the first chromatographic separation step is carried out using a stationary bed chromatography apparatus and the second chromatographic separation step is carried out using a stationary bed chromatography apparatus.

Alternatively, the first chromatographic separation step comprises introducing the feed mixture into a stationary bed apparatus and the second chromatographic separation step comprises introducing the intermediate product into a simulated or actual moving bed chromatography apparatus. Thus, typically the first chromatographic separation step is carried out using a stationary bed apparatus and the second chromatographic separation step is carried out using a simulated or actual moving bed chromatography apparatus.

Alternatively, the first chromatographic separation step comprises introducing the feed mixture into a simulated or actual moving bed chromatography apparatus and the second chromatographic separation step comprises introducing the intermediate product into a stationary bed chromatography apparatus. Thus, typically the first chromatographic separation step is carried out using a simulated or actual moving bed chromatography apparatus and the second chromatographic separation step is carried out using a stationary bed chromatography apparatus.

Alternatively, the first chromatographic separation step comprises introducing the feed mixture into a simulated or actual moving bed chromatography apparatus and the second chromatographic separation step comprises introducing the intermediate product into a simulated or actual moving bed chromatography apparatus. Thus, typically the first chromatographic separation step is carried out using a simulated or actual moving bed chromatography apparatus and the second chromatographic separation step is carried out using a simulated or actual moving bed chromatography apparatus.

Said first chromatographic separation step may consist of a single chromatographic separation or two or more chromatographic separations, provided that each separation uses as eluent a mixture of water and the first organic solvent.

Said second chromatographic separation step may consist of a single chromatographic separation or two or more chromatographic separations, provided that each separation uses as eluent a mixture of water and the second organic solvent.

Typically, the first and/or second chromatographic separation steps can involve the use of a single SMB separation step using conventional apparatus, such as for example depicted in FIG. 1. Separation in this manner may be referred to as "single pass" SMB. Typically, at least one of the first and/or second chromatographic separation steps involves at least one, for example one, "single pass" SMB step.

Alternatively, the first and/or second chromatographic separation steps can each involve the use of multiple SMB separations.

In one embodiment, the first chromatographic separation step and/or the second chromatographic separation step can be carried out as described in WO-A-2011/080503 and PCT/GB2012/051591, the entirety of which are incorporated herein by reference. Preferred process conditions specified in WO-A-2011/080503 and PCT/GB2012/051591 are preferred process conditions for this embodiment, and may be incorporated from WO-A-2011/080503 and PCT/GB2012/051591.

The process disclosed in WO-A-2011/080503 and PCT/GB2012/051591 involves introducing an input stream to a simulated or actual moving bed chromatography apparatus having a plurality of linked chromatography columns containing, as eluent, an aqueous organic solvent, wherein the apparatus has a plurality of zones comprising at least a first zone and second zone, each zone having an extract stream and a raffinate stream from which liquid can be collected from said plurality of linked chromatography columns, and wherein (a) a raffinate stream containing the PUFA product together with more polar components is collected from a column in the first zone and introduced to a nonadjacent column in the second zone, and/or (b) an extract stream containing the PUFA product together with less polar components is collected from a column in the second zone and introduced to a nonadjacent column in the first zone, said PUFA product being separated from different components of the input stream in each zone. Separation in this manner may be referred to as a "double pass" SMB process.

In this "double pass" SMB process, the term "zone" refers to a plurality of linked chromatography columns containing, as eluent, an aqueous organic solvent, and having one or more injection points for an input stream, one or more injection points for water and/or organic solvent, a raffinate take-off stream from which liquid can be collected from said plurality of linked chromatography columns, and an extract take-off stream from which liquid can be collected from said plurality of linked chromatography columns. Typically, each zone has only one injection point for an input stream. In one embodiment, each zone has only one injection point for the aqueous organic solvent eluent. In another embodiment, each zone has two or more injection points for water and/or organic solvent.

In this "double pass" SMB process, reference to an "input stream" refers to the feed mixture when the above-described SMB process is used in the first chromatographic separation step, and refers to the intermediate product when the above-described SMB process is used in the second chromatographic separation step.

In this "double pass" SMB process, reference to an "aqueous organic solvent" refers to the mixture of water and the first organic solvent when the above-described SMB process is used in the first chromatographic separation step, and refers to the mixture of water and the second organic solvent when the above-described SMB process is used in the second chromatographic separation step.

The term "raffinate" is well known to the person skilled in the art. In the context of actual and simulated moving bed chromatography it refers to the stream of components that move more rapidly with the liquid eluent phase compared with the solid adsorbent phase. Thus, a raffinate stream is typically enriched with more polar components, and depleted of less polar components compared with an input stream.

The term "extract" is well known to the person skilled in the art. In the context of actual and simulated moving bed chromatography it refers to the stream of components that move more rapidly with the solid adsorbent phase compared with the liquid eluent phase. Thus, an extract stream is typically enriched with less polar components, and depleted of more polar components compared with an input stream.

As used herein, the term "nonadjacent" refers to columns, in for example the same apparatus, separated by one or more columns, preferably 3 or more columns, more preferably 5 or more columns, most preferably about 5 columns.

Figure 11:
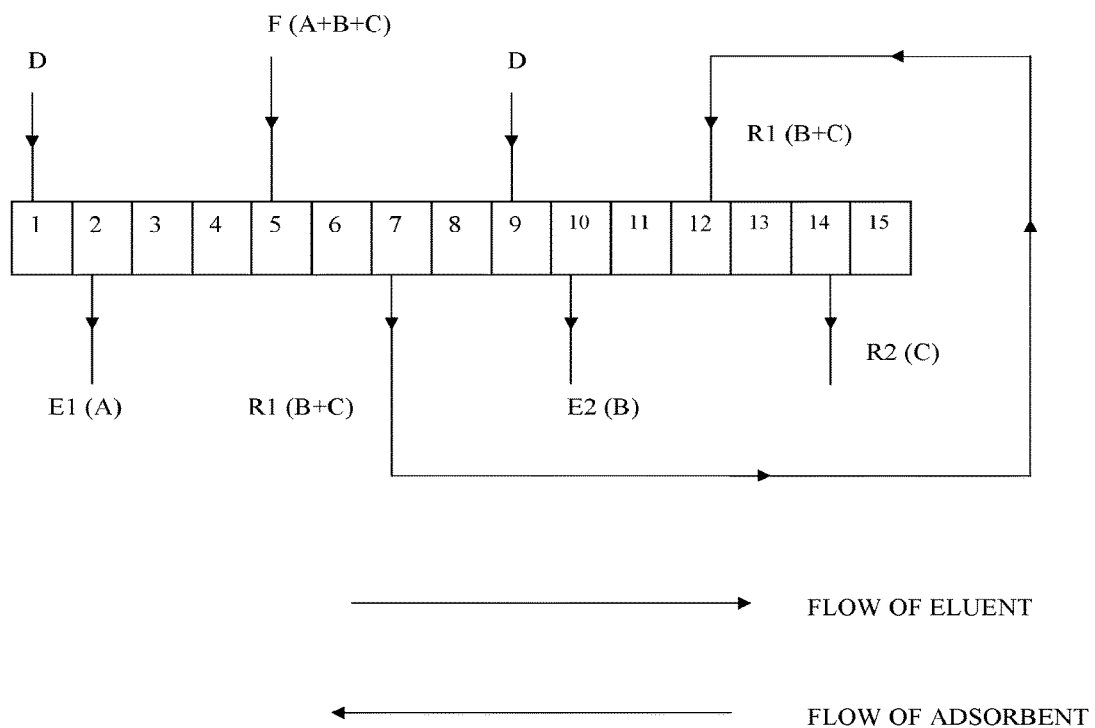
FIG. 11 illustrates a chromatographic separation step to separate EPA from faster and slower running impurities (i.e. more polar and less polar impurities).

The "double pass" SMB process is illustrated in FIG. 11. An input stream F comprising the PUFA product (B) and more polar (C) and less polar (A) components is introduced into the top of column 5 in the first zone. Aqueous organic solvent desorbent is introduced into the top of column 1 in the first zone. In the first zone, the less polar components (A) are removed as extract stream E1 from the bottom of column 2. The PUFA product (B) and more polar components (C)

are removed as raffinate stream R1 from the bottom of column 7. Raffinate stream R1 is then introduced into the second zone at the top of column 12. Aqueous organic solvent desorbent is introduced into the top of column 9 in the second zone. In the second zone, the more polar components (C) are removed as raffinate stream R2 at the bottom of column 14. The PUFA product (B) is collected as extract stream E2 at the bottom of column 10.

In this "double pass" SMB process, aqueous organic solvent is typically introduced into the top of column 1 in the first zone.

In this "double pass" SMB process, aqueous organic solvent is typically introduced into the top of column 9 in the second zone.

In this "double pass" SMB process, the input stream is typically introduced into the top of column 5 in the first zone.

In this "double pass" SMB process, a first raffinate stream is typically collected from the bottom of column 7 in the first zone and introduced into the top of column 12 in the second zone. The first raffinate stream may optionally be collected in a container before being introduced into column 12.

In this "double pass" SMB process, a first extract stream is typically removed from the bottom of column 2 in the first zone. The first extract stream may optionally be collected in a container and a portion reintroduced into the top of column 3 in the first zone. The rate of recycle of liquid collected via the extract stream from the first zone back into the first zone is the rate at which liquid is pumped from this container into the top of column 3.

In this "double pass" SMB process, a second raffinate stream is typically removed from the bottom of column 14 in the second zone.

In this "double pass" SMB process, a second extract stream is typically collected from the bottom of column 10 in the second zone. This second extract stream typically contains the PUFA product. The second extract stream may optionally be collected in a container and a portion reintroduced into the top of column 11 in the second zone. The rate of recycle of liquid collected via the extract stream from the second zone back into the second zone is the rate at which liquid is pumped from this container into the top of column 11.

In this "double pass" SMB process, the rate at which liquid collected via the extract stream from the first zone is recycled back into the first zone is typically faster than the rate at which liquid collected via the extract stream from the second zone is recycled back into the second zone. In this "double pass" SMB process, eluent is typically substantially the same in each zone.

Typically, at least one of the first and second chromatographic separation steps involves at least one, for example one, "double pass" SMB process as defined above.

In an alternative embodiment, the first chromatographic separation step and/or the second chromatographic separation step can be carried out as described in international patent application no. PCT/GB2012/051596 or PCT/GB2012/051597, the entirety of which are incorporated herein by reference. Such embodiments involve (i) purifying an input stream in a first SMB step in a simulated or actual moving bed chromatography apparatus having a plurality of linked chromatography columns containing, as eluent, an aqueous organic solvent, to obtain a first product; and (ii) purifying the first product obtained in (i) in a second SMB step using a simulated or actual moving bed chromatography apparatus having a plurality of linked chromatography columns containing, as eluent, an aqueous organic solvent, to obtain a second product; wherein (a) the first and second SMB steps are carried out sequentially on the same chromatography apparatus, the first product being recovered between the first and second SMB steps and the process conditions in the chromatography apparatus being adjusted between the first and second SMB steps such that the PUFA product is separated from different components of the feed mixture in each SMB step; or (b) the first and second SMB steps are carried out on separate first and second chromatography apparatuses respectively, the first product obtained from the first SMB step being introduced into the second chromatography apparatus, and the PUFA product being separated from different components of the feed mixture in each SMB step. Separation in this manner by be referred to as "back-to-back" SMB.

For the avoidance of doubt, if the first chromatographic separation step is a "back-to-back" SMB process along the above lines, the eluent in each of the SMB steps is a mixture of water and the first organic solvent. If the second chromatographic separation step is a "back-to-back" SMB process along the above lines, the eluent in each of the SMB steps is a mixture of water and the second organic solvent.

In this "back-to-back" SMB process, the term "simulated or actual moving bed chromatography apparatus" typically refers to a plurality of linked chromatography columns containing, as eluent, an aqueous organic solvent, and having one or more injection points for an input stream, one or more injection points for water and/or organic solvent, a raffinate take-off stream from which liquid can be collected from said plurality of linked chromatography columns, and an extract take-off stream from which liquid can be collected from said plurality of linked chromatography columns.

The chromatography apparatus used in this "back-to-back" SMB process has a single array of chromatography columns linked in series containing, as eluent, an aqueous organic solvent. Typically, each of the chromatography columns are linked to the two columns in the apparatus adjacent to that column. Thus, the output from a given column in the array is connected to the input of the adjacent column in the array, which is downstream with respect to the flow of eluent in the array. Thus, eluent can flow around the array of linked chromatography columns. Typically, none of the chromatography columns are linked to non-adjacent columns in the apparatus.

In this "back-to-back" SMB process, reference to an "input stream" refers to the feed mixture when the above-described SMB process is used in the first chromatographic separation step, and refers to the intermediate product when the above-described SMB process is used in the second chromatographic separation step.

In this "back-to-back" SMB process, reference to an "aqueous organic solvent" refers to the mixture of water and the first organic solvent when the above-described "back-to-back" SMB process is used in the first chromatographic separation step, and refers to the mixture of water and the second organic solvent when the above-described "back-to-back" SMB process is used in the second chromatographic separation step. The organic solvent used in the first and second SMB steps is the same. The organic solvent:water ratio used in the first and second SMB steps may be the same or different.

In this "back-to-back" SMB process, reference to a "second product" refers to the intermediate product when the above-described SMB process is used in the first chromatographic separation step, and refers to the PUFA product when the above-described SMB process is used in the second chromatographic separation step.

Typically in this "back-to-back" SMB process, each apparatus has only one injection point for an input stream. In one embodiment, each apparatus has only one injection point for the aqueous organic solvent eluent. In another embodiment, each apparatus has two or more injection points for water and/or organic solvent.

The term "raffinate" is well known to the person skilled in the art. In the context of actual and simulated moving bed chromatography it refers to the stream of components that move more rapidly with the liquid eluent phase compared with the solid adsorbent phase. Thus, a raffinate stream is typically enriched with more polar components, and depleted of less polar components compared with a feed stream.

The term "extract" is well known to the person skilled in the art. In the context of actual and simulated moving bed chromatography it refers to the stream of components that move more rapidly with the solid adsorbent phase compared with the liquid eluent phase. Thus, an extract stream is typically enriched with less polar components, and depleted of more polar components compared with a feed stream.

The number of columns used in each apparatus in this "back-to-back" SMB process is not particularly limited. A skilled person would easily be able to determine an appropriate number of columns to use. The number of columns is typically 4 or more, preferably 6 or more, more preferably 8 or more, for example 4, 5, 6, 7, 8, 9, or 10 columns. In a preferred embodiment, 5 or 6 columns, more preferably 6 columns are used. In another preferred embodiment, 7 or 8 columns, more preferably 8 columns are used. Typically, there are no more than 25 columns, preferably no more than 20, more preferably no more than 15.

In this "back-to-back" SMB process, the chromatographic apparatuses used in the first and second separation steps typically contain the same number of columns. For certain applications they may have different numbers of columns.

In this "back-to-back" SMB process, the columns in the chromatographic apparatuses used in the first and second SMB separation steps typically have identical dimensions but may, for certain applications, have different dimensions.

The flow rates to the columns are limited by maximum pressures across the series of columns and will depend on the column dimensions and particle size of the solid phases. One skilled in the art will easily be able to establish the required flow rate for each column dimension to ensure efficient desorption. Larger diameter columns will in general need higher flows to maintain linear flow through the columns.

In this "back-to-back" SMB process, for the typical column sizes outlined above, typically the flow rate of eluent into the chromatographic apparatus used in the first SMB separation step is from 1 to 4.5 L/min, preferably from 1.5 to 2.5 L/min. Typically, the flow rate of the extract from the chromatographic apparatus used in the first SMB separation step is from 0.1 to 2.5 L/min, preferably from 0.5 to 2.25 L/min. In embodiments where part of the extract from the first SMB separation step is recycled back into the apparatus used in the first SMB separation step, the flow rate of recycle is typically from 0.7 to 1.4 L/min, preferably about 1 L/min. Typically, the flow rate of the raffinate from the chromatographic apparatus used in the first SMB separation step is from 0.2 to 2.5 L/min, preferably from 0.3 to 2.0 L/min. In embodiments where part of the raffinate from the first SMB separation step is recycled back into the apparatus used in the first SMB separation step, the flow rate of recycle is typically from 0.3 to 1.0 L/min, preferably about 0.5 L/min. Typically, the flow rate of introduction of the input stream into the chromatographic apparatus used in the first SMB separation step is from 5 to 150 mL/min, preferably from 10 to 100 mL/min, more preferably from 20 to 60 mL/min.

In this "back-to-back" SMB process, for the typical column sizes outlined above, typically the flow rate of eluent into the chromatographic apparatus used in the second SMB separation step is from 1 to 4 L/min, preferably from 1.5 to 3.5 L/min. Typically, the flow rate of the extract from the chromatographic apparatus used in the second SMB separation step is from 0.5 to 2 L/min, preferably from 0.7 to 1.9 L/min. In embodiments where part of the extract from the second SMB separation step is recycled back into the apparatus used in the second SMB separation step, the flow rate of recycle is typically from 0.6 to 1.4 L/min, preferably from 0.7 to 1.1 L/min, more preferably about 0.9 L/min. Typically, the flow rate of the raffinate from the chromatographic apparatus used in the second SMB separation step is from 0.5 to 2.5 L/min, preferably from 0.7 to 1.8 L/min, more preferably about 1.4 L/min. In embodiments where part of the raffinate from the second SMB separation step is recycled back into the apparatus used in the second SMB separation step, the flow rate of recycle is typically from 0.3 to 1.0 L/min, preferably about 0.5 L/min.

As the skilled person will appreciate, references to rates at which liquid is collected or removed via the various extract and raffinate streams refer to volumes of liquid removed in an amount of time, typically L/minute. Similarly, references to rates at which liquid is recycled back into an apparatus, typically to an adjacent column in the apparatus, refer to volumes of liquid recycled in an amount of time, typically L/minute.

In this "back-to-back" SMB process, actual moving bed chromatography is preferred.

The step time, i.e. the time between shifting the points of injection of the input stream and eluent, and the various take off points of the collected fractions, is not particularly limited, and will depend on the number and dimensions of the columns used, and the flow rate through the apparatus. A skilled person would easily be able to determine appropriate step times to use in the process of the present invention. The step time is typically from 100 to 1000 seconds, preferably from 200 to 800 seconds, more preferably from about 250 to about 750 seconds. In some embodiments, a step time of from 100 to 400 seconds, preferably 200 to 300 seconds, more preferably about 250 seconds, is appropriate. In other embodiments, a step time of from 600 to 900 seconds, preferably 700 to 800 seconds, more preferably about 750 seconds is appropriate.

The "back-to-back" SMB process comprises a first and second SMB separation step.

These two steps can easily be carried out on a single chromatographic apparatus. Thus, in one embodiment, (a) the first and second SMB separation steps are carried out sequentially on the same chromatography apparatus, the first product being recovered between the first and second SMB separation steps and the process conditions in the chromatography apparatus being adjusted between the first and second SMB separation steps such that the PUFA product is separated from different components of the input stream in each separation step. A preferred embodiment of this "back-to-back" SMB process is shown as FIG. 10a. Thus, the first SMB separation step (left hand side) is carried out on an SMB apparatus having 8 columns. Between the first and second SMB separation steps the first product is recovered in, for example, a container, the process conditions in the chromatography apparatus are adjusted such that the PUFA product is separated from different components of the input stream in each SMB separation step. The second SMB separation step (right hand side) is then carried out on the same SMB apparatus having 8 columns.

In embodiment (a), adjusting the process conditions typically refers to adjusting the process conditions in the apparatus as a whole, i.e. physically modifying the apparatus so that the conditions are different. It does not refer to simply reintroducing the first product back into a different part of the same apparatus where the process conditions might happen to be different.

Alternatively, first and second separate chromatographic apparatuses can be used in the first and second SMB separation steps. Thus, in another embodiment, (b) the first and second SMB separation steps are carried out on separate first and second chromatography apparatuses respectively, the first product obtained from the first SMB separation step being introduced into the second chromatography apparatus, and the PUFA product being separated from different components of the input stream in each SMB separation step.

In embodiment (b), the two SMB separation steps may either be carried out sequentially or simultaneously.

Thus, in embodiment (b) in the case where the two SMB separation steps are carried out sequentially, the first and second SMB separation steps are carried out sequentially on separate first and second chromatography apparatuses respectively, the first product being recovered between the first and second SMB separation steps and the process conditions in the first and second SMB chromatography apparatuses being adjusted such that the PUFA product is separated from different components of the input stream in each separation step. A preferred embodiment of this "back-to-back" SMB separation process is shown as FIG. 10b. Thus, the first SMB separation step (left hand side) is carried out on an SMB apparatus having 8 columns, one to eight. Between the first and second SMB separation steps the first product is recovered, for example in a container, and then introduced into a second separate SMB apparatus. The second SMB separation step (right hand side) is carried out on the second separate SMB apparatus which has 8 columns, nine to sixteen. The process conditions in the two chromatography apparatuses are adjusted such that the PUFA product is separated from different components of the input stream in each SMB separation step.

In embodiment (b) in the case where the two SMB separation steps are carried our simultaneously, the first and second SMB separation steps are carried out on separate first and second chromatography apparatuses respectively, the first product being introduced into the chromatography apparatus used in the second SMB separation step, and the process conditions in the first and second chromatography apparatuses being adjusted such that the PUFA product is separated from different components of the input stream in each SMB separation step. A preferred embodiment of this "back-to-back" SMB separation process is shown as FIG. 10c. Thus, the first SMB separation step (left hand side) is carried out on an SMB apparatus having 8 columns, one to eight. The first product obtained in the first SMB separation step is then introduced into the second separate chromatography apparatus used in the second SMB separation step. The first product may be passed from the first SMB separation step to the second SMB separation step directly or indirectly, for example via a container. The second SMB separation step (right hand side) is carried out on the second separate SMB apparatus which has 8 columns, nine to sixteen. The process conditions in the two chromatography apparatuses are adjusted such that the PUFA product is separated from different components of the input stream in each separation step.

In embodiment (b) in the case where the two SMB separation steps are carried our simultaneously, eluent circulates separately in the two separate chromatographic apparatuses. Thus, eluent is not shared between the two separate chromatographic apparatuses other than what eluent may be present as solvent in the first product which is purified in the second SMB separation step, and which is introduced into the chromatographic apparatus used in the second SMB separation step. Chromatographic columns are not shared between the two separate chromatographic apparatuses used in the first and second SMB separation steps.

In this "back-to-back" SMB process, after the first product is obtained in the first SMB separation step, the aqueous organic solvent eluent may be partly or totally removed before the first product is purified in the second SMB separation step. Alternatively, the first product may be purified in the second SMB separation step without the removal of any solvent present.

As mentioned above, in this "back-to-back" SMB process the PUFA product is separated from different components of the input stream in each SMB separation step. In embodiment (a), the process conditions of the single SMB apparatus used in both SMB separation steps are adjusted between the first and second SMB separation steps such that the PUFA product is separated from different components of the input stream in each separation step. In embodiment (b), the process conditions in the two separate chromatography apparatuses used in the first and second SMB separation steps are set such that the PUFA product is separated from different components of the input stream in each separation step.

Thus, in this "back-to-back" SMB process the process conditions in the first and second SMB separation steps vary. The process conditions which vary may include, for example, the size of the columns used, the number of columns used, the packing used in the columns, the step time of the SMB apparatus, the temperature of the apparatus, the water:organic solvent ration of the eluent used in the separation steps, or the flow rates used in the apparatus, in particular the recycle rate of liquid collected via the extract or raffinate streams.

Preferably in this "back-to-back" SMB process, the process conditions which may vary are the water:organic solvent ratio of the eluent used in the SMB separation steps, and/or the recycle rate of liquid collected via the extract or raffinate streams in the SMB separation steps. Both of these options are discussed in more detail below.

In this "back-to-back" SMB process, the first product obtained in the first SMB separation step is typically enriched in the PUFA product compared to the input stream.

In this "back-to-back" SMB process, the first product obtained in the first SMB separation step is then introduced into the chromatographic apparatus used in the second SMB separation step.

In this "back-to-back" SMB process, the first product is typically collected as the raffinate or extract stream from the chromatographic apparatus used in the first SMB separation process.

Typically in this "back-to-back" SMB process, the first product is collected as the raffinate stream in the first SMB separation step, and the second product is collected as the extract stream in the second SMB separation step. Thus, the raffinate stream collected in the first SMB separation step is used as the input stream in the second SMB separation step. The raffinate stream collected in the first SMB separation step typically contains the second product together with more polar components.

Alternatively in this "back-to-back" SMB process, the first product is collected as the extract stream in the first SMB separation step, and the second product is collected as the raffinate stream in the second SMB separation step. Thus, the extract stream collected in the first SMB separation step is used as the input stream in the second SMB separation step. The extract stream collected in the first SMB separation step typically contains the second product together with less polar components.

In this "back-to-back" SMB process the PUFA product is separated from different components of the input stream in each SMB separation step. Typically, the components separated in each SMB separation step of the process of the present invention have different polarities.

Preferably in this "back-to-back" SMB process, the PUFA product is separated from less polar components of the input stream in the first SMB separation step, and the PUFA product is separated from more polar components of the input stream in the second SMB separation step.

Typically in this "back-to-back" SMB process, (a) part of the extract stream from the apparatus used in the first SMB separation step is recycled back into the apparatus used in the first SMB separation step; and/or (b) part of the raffinate stream from the apparatus used in the first SMB separation step is recycled back into the apparatus used in the first SMB separation step; and/or (c) part of the extract stream from the apparatus used in the second SMB separation step is recycled back into the apparatus used in the second SMB separation step; and/or (d) part of the raffinate stream from the apparatus used in the second SMB separation step is recycled back into the apparatus used in the second SMB separation step.

Preferably in this "back-to-back" SMB process, (a) part of the extract stream from the apparatus used in the first SMB separation step is recycled back into the apparatus used in the first SMB separation step; and (b) part of the raffinate stream from the apparatus used in the first SMB separation step is recycled back into the apparatus used in the first SMB separation step; and (c) part of the extract stream from the apparatus used in the second SMB separation step is recycled back into the apparatus used in the second SMB separation step; and (d) part of the raffinate stream from the apparatus used in the second SMB separation step is recycled back into the apparatus used in the second SMB separation step.

The recycle in this "back-to-back" SMB process involves feeding part of the extract or raffinate stream out of the chromatography apparatus used in the first or second SMB separation step back into the apparatus used in that SMB step, typically into an adjacent column. This adjacent column is the adjacent column which is downstream with respect to the flow of eluent in the system.

In this "back-to-back" SMB process the rate at which liquid collected via the extract or raffinate stream in the first or second SMB separation steps is recycled back into the chromatography apparatus used in that SMB step is the rate at which liquid collected via that stream is fed back into the apparatus used in that SMB step, typically into an adjacent column, i.e. the downstream column with respect to the flow of eluent in the system.

Figure 9:
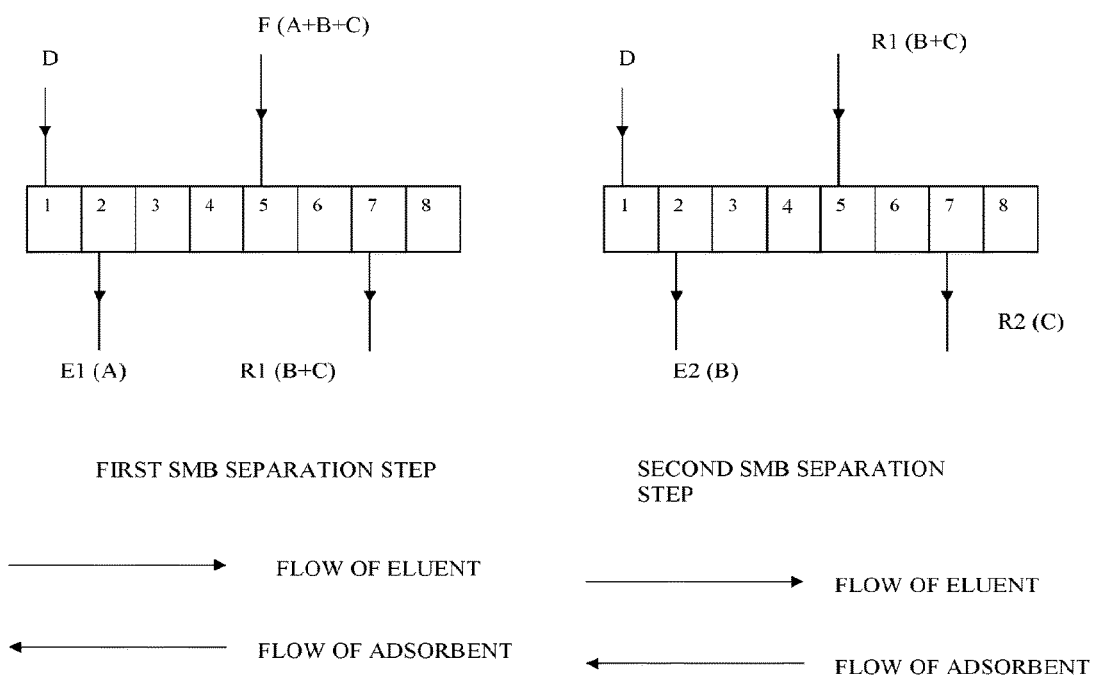
FIG. 9 illustrates a chromatographic separation step, which comprises two simulated or actual moving bed processes, to separate EPA from faster and slower running impurities (i.e. more polar and less polar impurities).

This can be seen with reference to FIG. 9. The rate of recycle of extract in the first SMB separation step is the rate at which extract collected from the bottom of column 2 of the chromatographic apparatus used in the first SMB separation step is fed into the top of column 3 of the chromatographic apparatus used in the first SMB separation step, i.e. the flow rate of liquid into the top of column 3 of the chromatographic apparatus used in the first SMB separation step.

In this "back-to-back" SMB process the rate of recycle of extract in the second SMB separation step is the rate at which extract collected at the bottom of column 2 of the chromatographic apparatus used in the second SMB separation step is fed into the top of column 3 of the chromatographic apparatus used in the second SMB separation step, i.e. the flow rate of liquid into the top of column 3 of the chromatographic apparatus used in the second SMB separation step.

In this "back-to-back" SMB process recycle of the extract and/or raffinate streams in the first and/or second SMB separation steps is typically effected by feeding the liquid collected via that stream in that SMB separation step into a container, and then pumping an amount of that liquid from the container back into the apparatus used in that SMB separation step, typically into an adjacent column. In this case, the rate of recycle of liquid collected via a particular extract or raffinate stream in the first and/or second SMB separation steps, typically back into an adjacent column, is the rate at which liquid is pumped out of the container back into the chromatography apparatus, typically into an adjacent column.

As the skilled person will appreciate, in this "back-to-back" SMB process the amount of liquid being introduced into a chromatography apparatus via the eluent and input streams is balanced with the amount of liquid removed from the apparatus, and recycled back into the apparatus.

Thus, in this "back-to-back" SMB process with reference to FIG. 9, for the extract stream, the flow rate of eluent (desorbent) into the chromatographic apparatus(es) used in the first and second SMB separation steps (D) is equal to the rate at which liquid collected via the extract stream in that SMB separation step accumulates in a container (E1 and E2) added to the rate at which extract is recycled back into the chromatographic apparatus used in that particular SMB separation step (D-E1 and D-E2).

In this "back-to-back" SMB process, for the raffinate stream from a SMB separation step, the rate at which extract is recycled back into the chromatographic apparatus used in that particular SMB separation step (D-E1 and D-E2) added to the rate at which feedstock is introduced into the chromatographic apparatus used in that particular SMB separation step (F and R1) is equal to the rate at which liquid collected via the raffinate stream in that particular SMB separation step accumulates in a container (R1 and R2) added to the rate at which raffinate is recycled back into the chromatographic apparatus used in that particular SMB separation step (D+F-E1-R1 and D+R1-E2-R2).

In this "back-to-back" SMB process, the rate at which liquid collected from a particular extract or raffinate stream from a chromatography apparatus accumulates in a container can also be thought of as the net rate of removal of that extract or raffinate stream from that chromatography apparatus.

Typically in this "back-to-back" SMB process, the rate at which liquid collected via the extract and raffinate streams in the first SMB separation step is recycled back into the apparatus used in that separation step is adjusted such that the PUFA product can be separated from different components of the input stream in each SMB separation step.

Typically in this "back-to-back" SMB process, the rate at which liquid collected via the extract and raffinate streams in the second SMB separation step is recycled back into the apparatus used in that SMB separation step is adjusted such that the PUFA product can be separated from different components of the input stream in each SMB separation step.

Preferably in this "back-to-back" SMB process, the rate at which liquid collected via the extract and raffinate streams in each SMB separation step is recycled back into the apparatus used in that SMB separation step is adjusted such that the PUFA product can be separated from different components of the input stream in each SMB separation step.

Typically in this "back-to-back" SMB process, the rate at which liquid collected via the extract stream in the first SMB separation step is recycled back into the chromatography apparatus used in the first SMB separation step differs from the rate at which liquid collected via the extract stream in the second SMB separation step is recycled back into the chromatography apparatus used in the second SMB separation step, and/or the rate at which liquid collected via the raffinate stream in the first SMB separation step is recycled back into the chromatography apparatus used in the first SMB separation step differs from the rate at which liquid collected via the raffinate stream in the second SMB separation step is recycled back into the chromatography apparatus used in the second SMB separation step.

Varying the rate at which liquid collected via the extract and/or raffinate streams in the first or second SMB separation steps is recycled back into the apparatus used in that particular SMB separation step has the effect of varying the amount of more polar and less polar components present in the extract and raffinate streams. Thus, for example, a lower extract recycle rate results in fewer of the less polar components in that SMB separation step being carried through to the raffinate stream. A higher extract recycle rate results in more of the less polar components in that SMB separation step being carried through to the raffinate stream.

Figure 6:
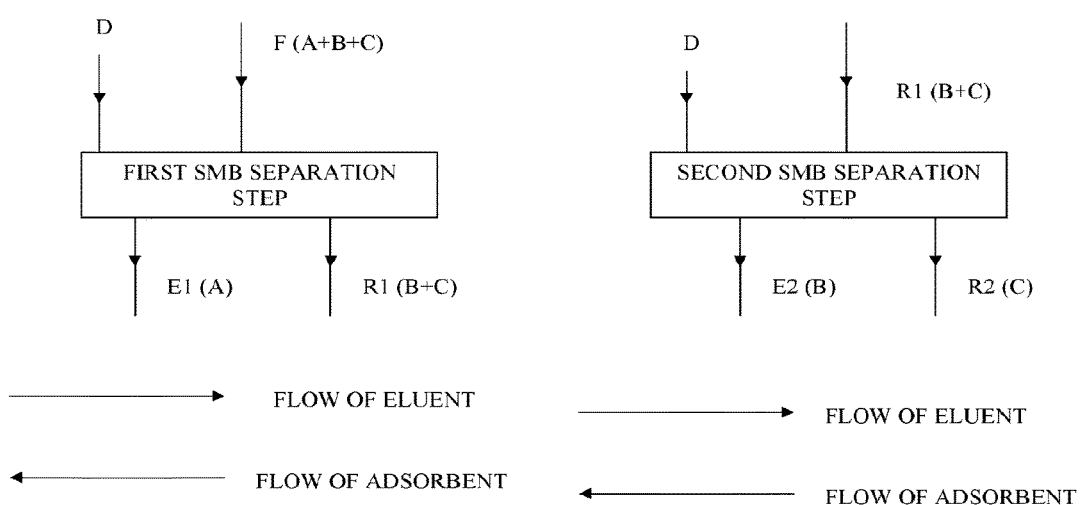
FIG. 6 illustrates a chromatographic separation step, which comprises two simulated or actual moving bed processes, to separate EPA from faster and slower running impurities (i.e. more polar and less polar impurities).

This can be seen, for example, in FIG. 6. The rate at which liquid collected via the extract stream in the first SMB separation step is recycled back into the chromatographic apparatus used in that SMB separation step (D-E1) will affect to what extent any of component A is carried through to the raffinate stream in the first SMB separation step (R1).

Typically in this "back-to-back" SMB process, the rate at which liquid collected via the extract stream in the first SMB separation step is recycled back into the chromatographic apparatus used in the first SMB separation step is faster than the rate at which liquid collected via the extract stream in the second SMB separation step is recycled back into the chromatographic apparatus used in the second SMB separation step. Preferably, a raffinate stream containing the second product together with more polar components is collected from the first SMB separation step and purified in a second SMB separation step, and the rate at which liquid collected via the extract stream in the first SMB separation step is recycled back into the chromatographic apparatus used in the first SMB separation step is faster than the rate at which liquid collected via the extract stream in the second SMB separation step is recycled back into the chromatographic apparatus used in the second SMB separation step.

Alternatively in this "back-to-back" SMB process, the rate at which liquid collected via the extract stream in the first SMB separation step is recycled back into the chromatographic apparatus used in the first SMB separation step is slower than the rate at which liquid collected via the extract stream in the second SMB separation step is recycled back into the chromatographic apparatus used in the second SMB separation step.

Typically in this "back-to-back" SMB process, the rate at which liquid collected via the raffinate stream in the first SMB separation step is recycled back into the chromatographic apparatus used in the first separation step is faster than the rate at which liquid collected via the raffinate stream in the second SMB separation step is recycled back into the chromatographic apparatus used in the second SMB separation step. Preferably, an extract stream containing the second product together with less polar components is collected from the first SMB separation step and purified in a second SMB separation step, and the rate at which liquid collected via the raffinate stream in the first SMB separation step is recycled back into the chromatographic apparatus used in the first SMB separation step is faster than the rate at which liquid collected via the raffinate stream in the second SMB separation step is recycled back into the chromatographic apparatus used in the second SMB separation step.

Alternatively in this "back-to-back" SMB process, the rate at which liquid collected via the raffinate stream in the first SMB separation step is recycled back into the chromatographic apparatus used in the first SMB separation step is slower than the rate at which liquid collected via the raffinate stream in the second SMB separation step is recycled back into the chromatographic apparatus used in the second SMB separation step.

In this "back-to-back" SMB process, where recycle rates are adjusted such that the PUFA product can be separated from different components of the input stream in each SMB separation step, the water:organic solvent ratio of the eluents used in each SMB separation step may be the same or different. Typical water:organic solvent ratios of the eluent in each SMB separation step are as defined above.

Typically in this "back-to-back" SMB process, the aqueous organic solvent eluent used in each SMB separation step has a different water:organic solvent ratio. The organic solvent used in each SMB separation step is the same. The water:organic solvent ratio used in each SMB separation step is preferably adjusted such that the PUFA product can be separated from different components of the input stream in each SMB separation step.

In this "back-to-back" SMB process, the eluting power of the eluent used in each of the SMB separation steps is typically different. Preferably, the eluting power of the eluent used in the first SMB separation step is greater than that of the eluent used in the second SMB separation step. In practice this is achieved by varying the relative amounts of water and organic solvent used in each SMB separation step.

Depending on the choice of organic solvent, they may be more powerful desorbers than water. Alternatively, they may be less powerful desorbers than water. Acetonitrile and alcohols, for example, are more powerful desorbers than water. Thus, when the aqueous organic solvent is aqueous alcohol or acetonitrile, the amount of alcohol or acetonitrile in the eluent used in the first SMB separation step is typically greater than the amount of alcohol or acetonitrile in the eluent used in the second SMB separation step.

Typically in this "back-to-back" SMB process, the water:organic solvent ratio of the eluent in the first SMB separation step is lower than the water:organic solvent ratio of the eluent in the second SMB separation step. Thus, the eluent in the first SMB separation step typically contains more organic solvent than the eluent in the second SMB separation step.

It will be appreciated that the ratios of water and organic solvent in each SMB separation step referred to above are average ratios within the totality of the chromatographic apparatus.

Typically in this "back-to-back" SMB process, the water:organic solvent ratio of the eluent in each SMB separation step is controlled by introducing water and/or organic solvent into one or more columns in the chromatographic apparatuses used in the SMB separation steps. Thus, for example, to achieve a lower water:organic solvent ratio in the first SMB separations step than in the second SMB separation step, water is typically introduced more slowly into the chromatographic apparatus used in the first SMB separation step than in the second SMB separation step.

Typically in this "back-to-back" SMB process, essentially pure organic solvent and essentially pure water may be introduced at different points in the chromatographic apparatus used in each SMB separation step. The relative flow rates of these two streams will determine the overall solvent profile in the chromatographic apparatus. Alternatively in this "back-to-back" SMB process, different mixtures of the organic solvent and water may be introduced at different points in each chromatographic apparatus used in each SMB separation step. That will involve introducing two or more different mixtures of the organic solvent and water into the chromatographic apparatus used in a particular SMB separation step, each organic solvent/water mixture having a different organic solvent:water ratio. The relative flow rates and relative concentrations of the organic solvent/water mixtures in this "back-to-back" SMB process will determine the overall solvent profile in the chromatographic apparatus used in that SMB separation step.

Preferably in this "back-to-back" SMB process, either (1) the first product containing the second product together with more polar components is collected as the raffinate stream in the first SMB separation step, and the second product is collected as the extract stream in the second SMB separation step; or (2) the first product containing the second product together with less polar components is collected as the extract stream in the first SMB separation step, and the second product is collected as the raffinate stream in the second SMB separation step.

Option (1) is suitable for purifying EPA from an input stream.

Figure 2:
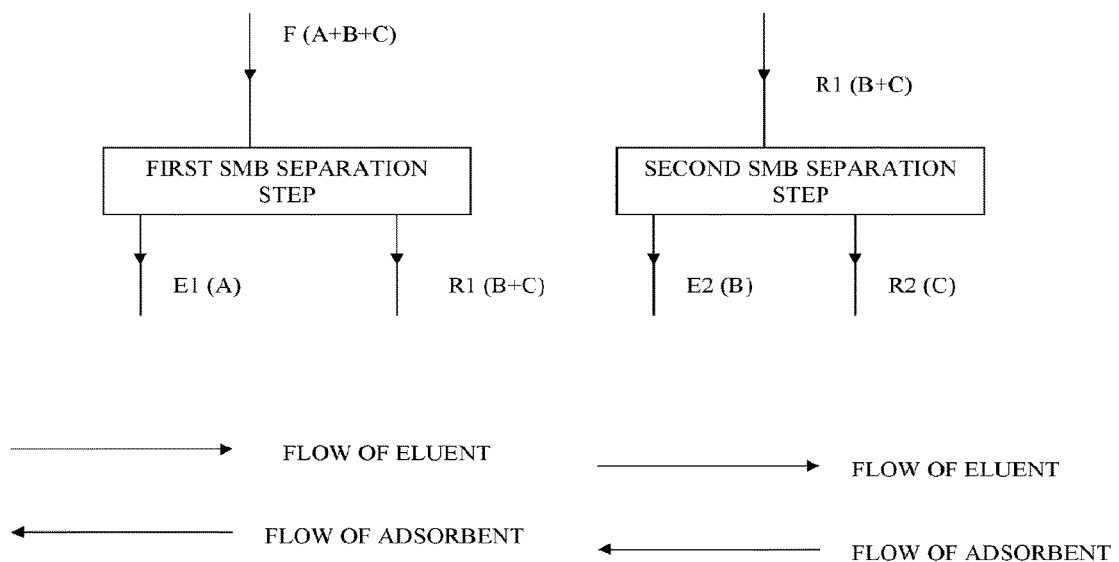
FIG. 2 illustrates a chromatographic separation step, which comprises two simulated or actual moving bed processes, to separate EPA from faster and slower running impurities (i.e. more polar and less polar impurities).

Option (1) is illustrated in FIG. 2. An input stream F comprising the second product (B) and more polar (C) and less polar (A) components is purified in the first SMB separation step. In the first SMB separation step, the less polar components (A) are removed as extract stream E1. The second product (B) and more polar components (C) are collected as raffinate stream R1. Raffinate stream R1 is the first product which is then purified in the second SMB separation step. In the second SMB separation step, the more polar components (C) are removed as raffinate stream R2. The second product (B) is collected as extract stream E2.

Figure 4:
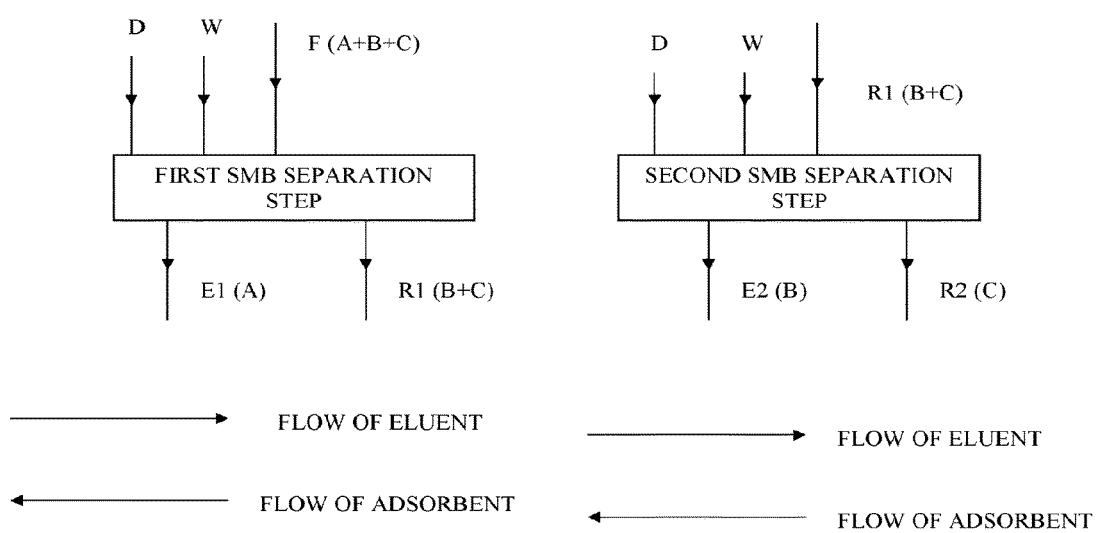
FIG. 4 illustrates a chromatographic separation step, which comprises two simulated or actual moving bed processes, to separate EPA from faster and slower running impurities (i.e. more polar and less polar impurities).

Option (1) is illustrated in more detail in FIG. 4. FIG. 4 is identical to FIG. 2, except that the points of introduction of the organic solvent desorbent (D) and water (W) into each chromatographic apparatus are shown. The organic solvent desorbent (D) and water (W) together make up the eluent. The (D) phase is typically essentially pure organic solvent, but may, in certain embodiments be an organic solvent/water mixture comprising mainly organic solvent. The (W) phase is typically essentially pure water, but may, in certain embodiments be an organic solvent/water mixture comprising mainly water, for example a 98% water/2% methanol mixture.

A further illustration of option (1) is shown in FIG. 6. Here there is no separate water injection point, and instead an aqueous organic solvent desorbent is injected at (D).

In option (1), the separation into raffinate and extract stream can be aided by varying the desorbing power of the eluent within each chromatographic apparatus. This can be achieved by introducing the organic solvent (or organic solvent rich) component of the eluent and the water (or water rich) component at different points in each chromatographic apparatus. Thus, typically, the organic solvent is introduced upstream of the extract take-off point and the water is introduced between the extract take-off point and the point of introduction of the feed into the chromatographic apparatus, relative to the flow of eluent in the system. This is shown in FIG. 4.

Typically, in option (1), the aqueous organic solvent eluent used in the first SMB separation step contains more organic solvent than the eluent used in the second SMB separation step, i.e. the water:organic solvent ratio in the first SMB separation step is lower than the water:organic solvent ratio in the second SMB separation step.

In option (1), the SMB separation can be aided by varying the rates at which liquid collected via the extract and raffinate streams in the first and second SMB separation steps is recycled back into the chromatographic apparatus used in that SMB separation step.

Typically, in option (1), the rate at which liquid collected via the extract stream in the first SMB separation step is recycled back into the chromatographic apparatus used in the first SMB separation step is faster than the rate at which liquid collected via the extract stream in the second SMB separation step is recycled back into the chromatographic apparatus used in the second SMB separation step.

In option (1) the first raffinate stream in the first SMB separation step is typically removed downstream of the point of introduction of the input stream into the chromatographic apparatus used in the first SMB separation step, with respect to the flow of eluent.

In option (1), the first extract stream in the first SMB separation step is typically removed upstream of the point of introduction of the input stream into the chromatographic apparatus used in the first SMB separation step, with respect to the flow of eluent.

In option (1), the second raffinate stream in the second SMB separation step is typically removed downstream of the point of introduction of the first product into the chromatographic apparatus used in the second SMB separation step, with respect to the flow of eluent.

In option (1), the second extract stream in the second SMB separation step is typically collected upstream of the point of introduction of the first product into the chromatographic apparatus used in the second SMB separation step, with respect to the flow of eluent.

Typically in option (1), the organic solvent or aqueous organic solvent is introduced into the chromatographic apparatus used in the first SMB separation step upstream of the point of removal of the first extract stream, with respect to the flow of eluent.

Typically in option (1), when water is introduced into the chromatographic apparatus used in the first SMB separation step, the water is introduced into the chromatographic apparatus used in the first SMB separation step upstream of the point of introduction of the input stream but downstream of the point of removal of the first extract stream, with respect to the flow of eluent.

Typically in option (1), the organic solvent or aqueous organic solvent is introduced into the chromatographic apparatus used in the second SMB separation step upstream of the point of removal of the second extract stream, with respect to the flow of eluent.

Typically in option (1), when water is introduced into the chromatographic apparatus used in the second SMB separation step, the water is introduced into the chromatographic apparatus used in the second SMB separation step upstream of the point of introduction of the first product but downstream of the point of removal of the second extract stream, with respect to the flow of eluent.

Option (2) is suitable for purifying DHA from an input stream.

Figure 3:
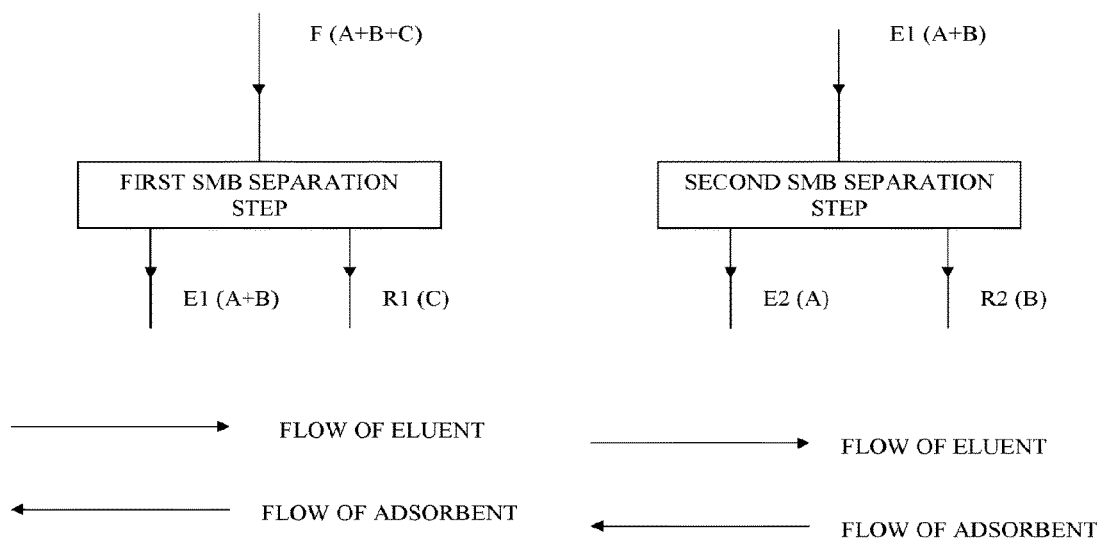
FIG. 3 illustrates a chromatographic separation step, which comprises two simulated or actual moving bed processes, to separate DHA from faster and slower running impurities (i.e. more polar and less polar impurities).

Option (2) is illustrated in FIG. 3. An input stream F comprising the second product (B) and more polar (C) and less polar (A) components is purified in the first SMB separation step. In the first SMB separation step, the more polar components (C) are removed as raffinate stream R1. The second product (B) and less polar components (A) are collected as extract stream E1. Extract stream E1 is the first product which is then purified in the second SMB separation step. In the second SMB separation step, the less polar components (A) are removed as extract stream E2. The second product (B) is collected as raffinate stream R2.

Figure 5:
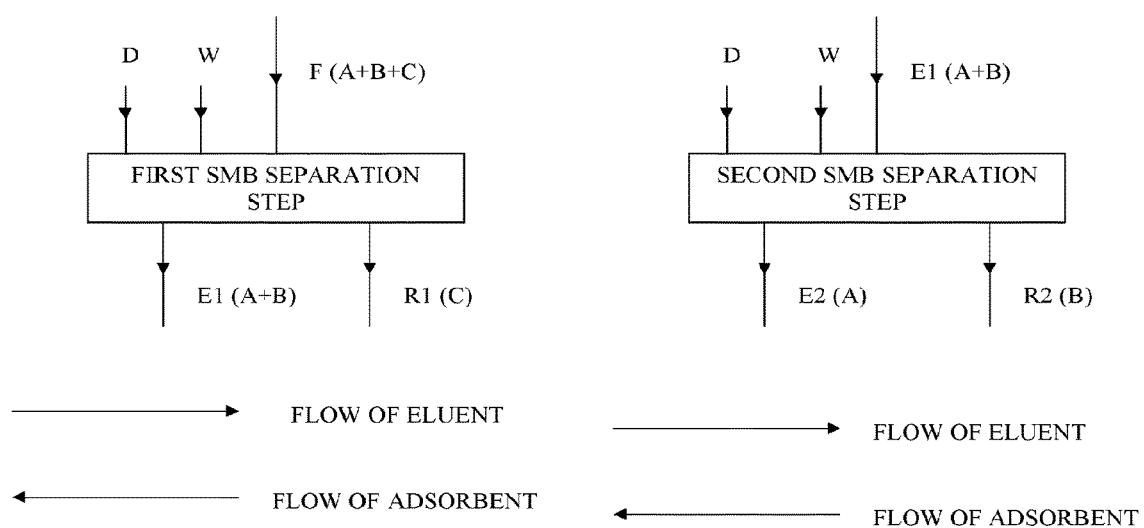
FIG. 5 illustrates a chromatographic separation step, which comprises two simulated or actual moving bed processes, to separate DHA from faster and slower running impurities (i.e. more polar and less polar impurities).

Option (2) is illustrated in more detail in FIG. 5. FIG. 5 is identical to FIG. 3, except that the points of introduction of the organic solvent desorbent (D) and water (W) into each chromatographic apparatus are shown. As above, the (D) phase is typically essentially pure organic solvent, but may, in certain embodiments be an organic solvent/water mixture comprising mainly organic solvent. The (W) phase is typically essentially pure water, but may, in certain embodiments be an organic solvent/water mixture comprising mainly water, for example a 98% water/2% methanol mixture.

Figure 7:
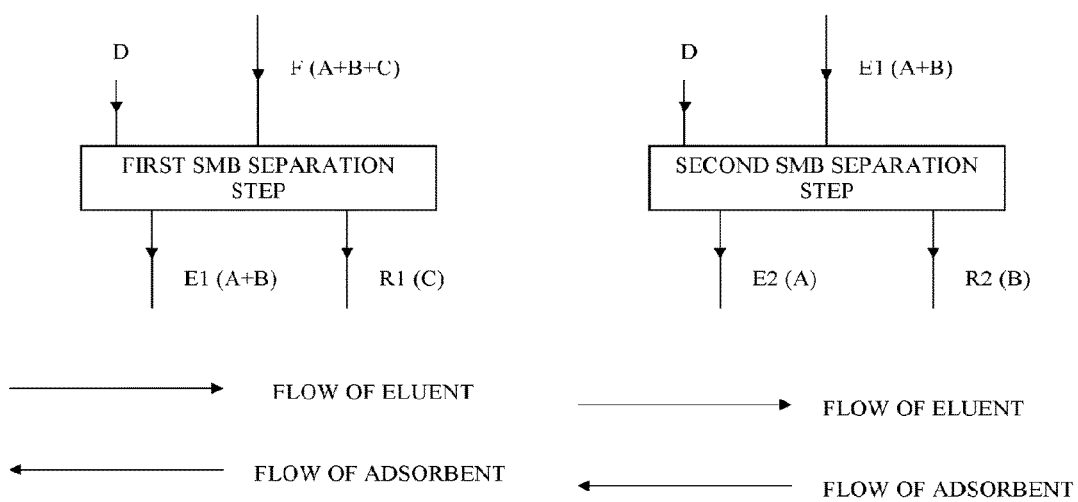
FIG. 7 illustrates a chromatographic separation step, which comprises two simulated or actual moving bed processes, to separate DHA from faster and slower running impurities (i.e. more polar and less polar impurities).

A further illustration of option (2) is shown in FIG. 7. Here there is no separate water injection point, and instead an aqueous organic solvent desorbent is injected at (D).

Typically in option (2), the rate at which liquid collected via the raffinate stream in the first SMB separation step is reintroduced into the chromatographic apparatus used in the first SMB separation step is faster than the rate at which liquid collected via the raffinate stream in the second SMB separation step is reintroduced into the chromatographic apparatus used in the second SMB separation step.

Typically in option (2), the aqueous organic solvent eluent used in the first SMB separation step contains less organic solvent than the eluent used in the second SMB separation step, i.e. the water:organic solvent ratio in the first SMB separation step is higher than in the second SMB separation step.

In option (2) the first raffinate stream in the first separation step is typically removed downstream of the point of introduction of the input stream into the chromatographic apparatus used in the first SMB separation step, with respect to the flow of eluent.

In option (2), the first extract stream in the first SMB separation step is typically removed upstream of the point of introduction of the input stream into the chromatographic apparatus used in the first SMB separation step, with respect to the flow of eluent.

In option (2), the second raffinate stream in the second SMB separation step is typically removed downstream of the point of introduction of the first product into the chromatographic apparatus used in the second SMB separation step, with respect to the flow of eluent.

In option (2), the second extract stream in the second SMB separation step is typically collected upstream of the point of introduction of the first product into the chromatographic apparatus used in the second SMB separation step, with respect to the flow of eluent.

Typically in option (2), the organic solvent or aqueous organic solvent is introduced into the chromatographic apparatus used in the first SMB separation step upstream of the point of removal of the first extract stream, with respect to the flow of eluent.

Typically in option (2), when water is introduced into the chromatographic apparatus used in the first SMB separation step, the water is introduced into the chromatographic apparatus used in the first SMB separation step upstream of the point of introduction of the input stream but downstream of the point of removal of the first extract stream, with respect to the flow of eluent.

Typically in option (2), the organic solvent or aqueous organic solvent is introduced into the chromatographic apparatus used in the second SMB separation step upstream of the point of removal of the second extract stream, with respect to the flow of eluent.

Typically in option (2), when water is introduced into the chromatographic apparatus used in the second SMB separation step, the water is introduced into the chromatographic apparatus used in the second SMB separation step upstream of the point of introduction of the first product but downstream of the point of removal of the second extract stream, with respect to the flow of eluent.

In this "back-to-back" SMB process, each of the simulated or actual moving bed chromatography apparatus used in the first and second SMB separation steps preferably consist of eight chromatographic columns. These are referred to as columns 1 to 8. In each apparatus the eight columns are arranged in series so that the bottom of column 1 is linked to the top of column 2, the bottom of column 2 is linked to the top of column 3 . . . etc . . . and the bottom of column 8 is linked to the top of column 1. These linkages may optionally be via a holding container, with a recycle stream into the next column. The flow of eluent through the system is from column 1 to column 2 to column 3 etc. The effective flow of adsorbent through the system is from column 8 to column 7 to column 6 etc.

Figure 8:
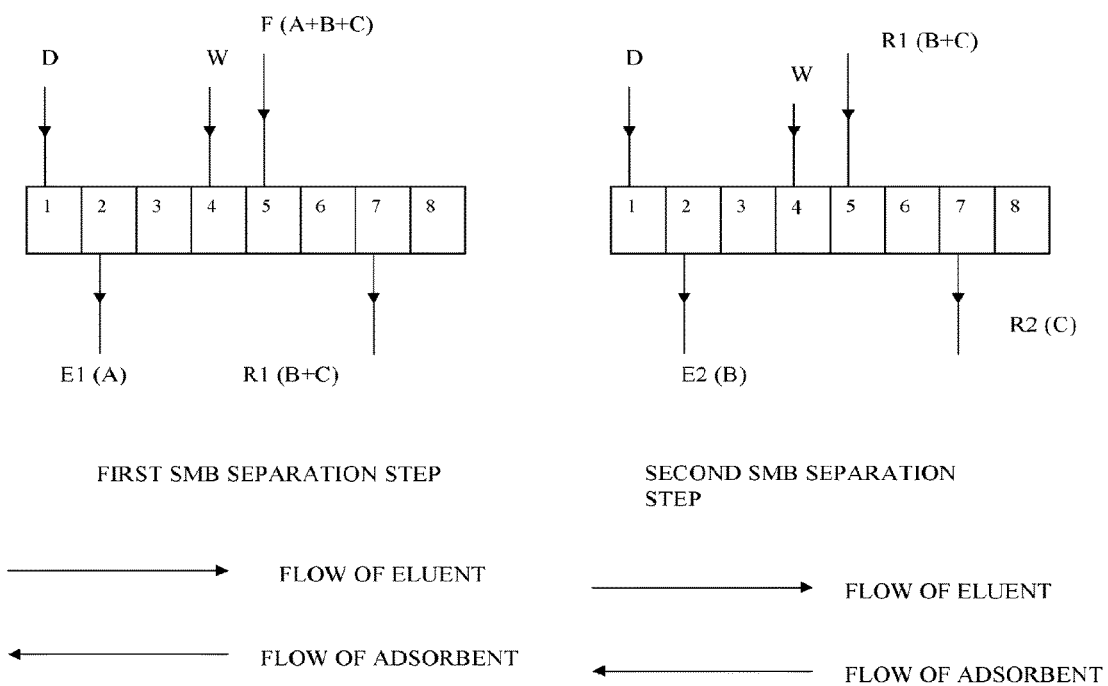
FIG. 8 illustrates a chromatographic separation step, which comprises two simulated or actual moving bed processes, to separate EPA from faster and slower running impurities (i.e. more polar and less polar impurities).

This is illustrated in FIG. 8. An input stream F comprising the second product (B) and more polar (C) and less polar (A) components is introduced into the top of column 5 in the chromatographic apparatus used in the first SMB separation step. Organic solvent desorbent is introduced into the top of column 1 of the chromatographic apparatus used in the first SMB separation step. Water is introduced into the top of column 4 of the chromatographic apparatus used in the first SMB separation step. In the first SMB separation step, the less polar components (A) are removed as extract stream E1 from the bottom of column 2. The second product (B) and more polar components (C) are removed as raffinate stream R1 from the bottom of column 7. Raffinate stream R1 is the first product which is then purified in the second SMB separation step, by being introduced into the chromatographic apparatus used in the second SMB separation step at the top of column 5. Organic solvent desorbent is introduced into the top of column 1 in the chromatographic apparatus used in the second SMB separation step. Water is introduced into the top of column 4 in the chromatographic apparatus used in the second SMB separation step. In the second SMB separation step, the more polar components (C) are removed as raffinate stream R2 at the bottom of column 7. The second product (B) is collected as extract stream E2 at the bottom of column 2.

In the "back-to-back" SMB process shown in FIG. 8, organic solvent is typically introduced into the top of column 1 of the chromatographic apparatus used in the first SMB separation step.

In the "back-to-back" SMB process shown in FIG. 8, water is typically introduced into the top of column 4 of the chromatographic apparatus used in the first SMB separation step.

In the "back-to-back" SMB process shown in FIG. 8, organic solvent is typically introduced into the top of column 1 of the chromatographic apparatus used in the second SMB separation step.

In the "back-to-back" SMB process shown in FIG. 8, organic solvent is typically introduced into the top of column 4 of the chromatographic apparatus used in the second SMB separation step.

In the "back-to-back" SMB process shown in FIG. 8, the input stream is typically introduced into the top of column 5 of the chromatographic apparatus used in the first SMB separation step.

In the "back-to-back" SMB process shown in FIG. 8, a first raffinate stream is typically collected as the first product from the bottom of column 7 of the chromatographic apparatus used in the first SMB separation step. This first product is then purified in the second SMB separation step and is typically introduced into the top of column 5 of the chromatographic apparatus used in the second SMB separation step. The first raffinate stream may optionally be collected in a container before being purified in the second SMB separation step.

In the "back-to-back" SMB process shown in FIG. 8, a first extract stream is typically removed from the bottom of column 2 of the chromatographic apparatus used in the first SMB separation step. The first extract stream may optionally be collected in a container and reintroduced into the top of column 3 of the chromatographic apparatus used in the first SMB separation step.

In the "back-to-back" SMB process shown in FIG. 8, a second raffinate stream is typically removed from the bottom of column 7 of the chromatographic apparatus used in the second SMB separation step.

In the "back-to-back" SMB process shown in FIG. 8, a second extract stream is typically collected from the bottom of column 2 of the chromatographic apparatus used in the second SMB separation step. This second extract stream typically contains the second product. The second extract stream may optionally be collected in a container and reintroduced into the top of column 3 of the chromatographic apparatus used in the second SMB separation step.

In the "back-to-back" SMB process shown in FIG. 8, the eluent used is typically as defined above.

Typically, in this "back-to-back" SMB process, the water:organic solvent ratio in the chromatographic apparatus used in the first SMB separation step is lower than the water:organic solvent ratio in the chromatographic apparatus used in the second SMB separation step. Thus, the eluent in the first SMB separation step typically contains more organic solvent than the eluent used in the second SMB separation step.

In this "back-to-back" SMB process, the water:organic solvent ratio in the first SMB separation step is typically from 0.5:99.5 to 1.5:98.5 parts by volume. The water:organic solvent ratio in the second SMB separation step is typically from 2:98 to 6:94 parts by volume.

Figure 10:
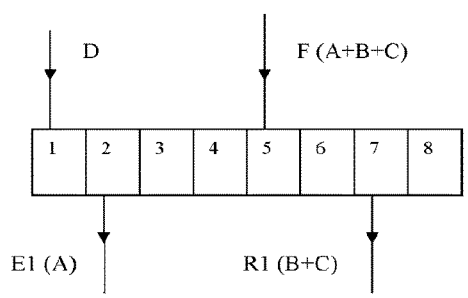
FIG. 10 illustrates three ways in which a chromatographic separation step which comprises two simulated or actual moving bed processes may be carried out.
Figure 10:
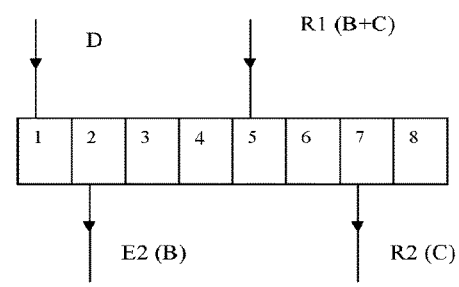
Figure 10:
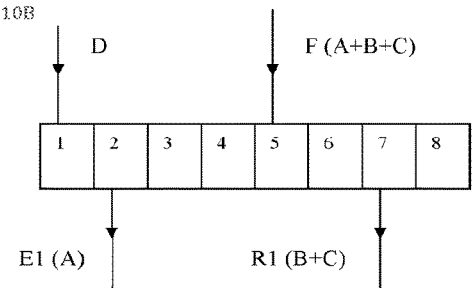
Figure 10:
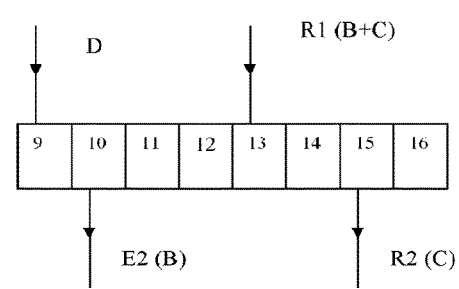
Figure 10:
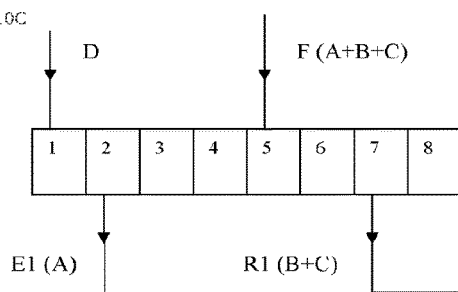
Figure 10:
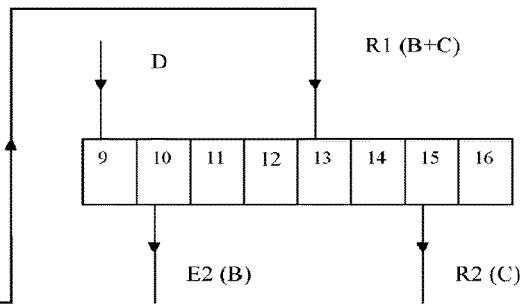

In this "back-to-back" SMB process, although the apparatus of FIG. 8 is configured as shown in FIG. 10*a*, the configurations shown in FIGS. 10*b* and 10*c* could also be used.

This "back-to-back" SMB process is also illustrated in FIG. 9. An input stream F comprising the second product (B) and more polar (C) and less polar (A) components is introduced into the top of column 5 in the chromatographic apparatus used in the first SMB separation step. Aqueous organic solvent desorbent is introduced into the top of column 1 in the chromatographic apparatus used in the first SMB separation step. In the first SMB separation step, the less polar components (A) are removed as extract stream E1 from the bottom of column 2. The second product (B) and more polar components (C) are removed as raffinate stream R1 from the bottom of column 7. Raffinate stream R1 is the first product which is purified in the second SMB separation step by being introduced into the top of column 4 of the chromatographic apparatus used in the second SMB separation step. Aqueous organic solvent desorbent is introduced into the top of column 1 in the chromatographic apparatus used in the second SMB separation step. In the second SMB separation step, the more polar components (C) are removed as raffinate stream R2 at the bottom of column 7. The second product (B) is collected as extract stream E2 at the bottom of column 2.

In the "back-to-back" SMB process shown in FIG. 9, aqueous organic solvent is typically introduced into the top of column 1 in the chromatographic apparatus used in the first SMB separation step.

In the "back-to-back" SMB process shown in FIG. 9, aqueous organic solvent is typically introduced into the top of column 9 in the chromatographic apparatus used in the second SMB separation step.

In the "back-to-back" SMB process shown in FIG. 9, the input stream is typically introduced into the top of column 5 in the chromatographic apparatus used in the first SMB separation step.

In the "back-to-back" SMB process shown in FIG. 9, a first raffinate stream is typically collected as the first product from the bottom of column 7 of the chromatographic apparatus used in the first SMB separation step. This first product is then purified in the second SMB separation step and is typically introduced into the top of column 5 of the chromatographic apparatus used in the second SMB separation step. The first raffinate stream may optionally be collected in a container before being purified in the second SMB separation step.

In the "back-to-back" SMB process shown in FIG. 9, a first extract stream is typically removed from the bottom of column 2 of the chromatographic apparatus used in the first SMB separation step. The first extract stream may optionally be collected in a container and a portion reintroduced into the top of column 3 of the chromatographic apparatus used in the first SMB separation step. The rate of recycle of liquid collected via the extract stream in the first SMB separation step back into the chromatographic apparatus used in the first SMB separation step is the rate at which liquid is pumped from this container into the top of column 3.

In the "back-to-back" SMB process shown in FIG. 9, a second raffinate stream is typically removed from the bottom of column 7 of the chromatographic apparatus used in the first SMB separation step.

In the "back-to-back" SMB process shown in FIG. 9, a second extract stream is typically collected from the bottom of column 2 of the chromatographic apparatus used in the first SMB separation step. This second extract stream typically contains the second product. The second extract stream may optionally be collected in a container and a portion reintroduced into the top of column 3 of the chromatographic apparatus used in the first SMB separation step. The rate of recycle of liquid collected via the extract stream from the second SMB separation step back into the chromatographic apparatus used in the second SMB separation step is the rate at which liquid is pumped from this container into the top of column 3.

In the "back-to-back" SMB process shown in FIG. 9, the eluent used is as defined above.

Typically, in this "back-to-back" SMB process, the water: organic solvent ratio in the chromatographic apparatus used in the first SMB separation step is lower than the water: organic solvent ratio in the chromatographic apparatus used in the second SMB separation step. Thus, the eluent used in the first SMB separation step typically contains more organic solvent than the eluent used in the second SMB separation step.

In this "back-to-back" SMB process, the water:organic solvent ratio in the first SMB separation step is typically from 0.5:99.5 to 1.5:98.5 parts by volume. The water: organic solvent ratio in the second SMB separation step is typically from 2:98 to 6:94 parts by volume.

In this "back-to-back" SMB process, the rate at which liquid collected via the extract stream from the first SMB separation step is recycled back into the chromatographic apparatus used in the first SMB separation step is typically faster than the rate at which liquid collected via the extract stream from the second SMB separation step is recycled back into the chromatographic apparatus used in the second SMB separation step. In this case, the aqueous organic solvent eluent is typically substantially the same in each SMB separation step.

In this "back-to-back" SMB process, although the apparatus of FIG. 9 is configured as shown in FIG. 10a, the configurations shown in FIGS. 10b and 10c could also be used.

Typically, at least one of the first and second chromatographic separation steps involve at least one, for example one, "back-to-back" SMB process as defined above.

Typically, the PUFA product is separated from different components of the feed mixture in each chromatographic separation step.

Typically, the PUFA product is separated from one or more of the C18 fatty acid impurities disclosed above in the first and/or second separation steps. Typically the PUFA product is separated from one or more of the C18 fatty acid impurities discussed above in only one of the first and second separation steps.

More typically, the PUFA product is separated from ALA, ALA mono-, di- and triglycerides and ALA $C_1$-$C_4$ alkyl esters in the first and/or second separation steps.

More typically, the PUFA product is separated from GLA, GLA mono-, di- and triglycerides and GLA $C_1$-$C_4$ alkyl esters in the first and/or second separation steps.

Preferably, the PUFA product is separated from C18 fatty acids, C18 fatty acid mono-, di- and triglycerides and C18 fatty acid alkyl esters in the first and/or second separation steps.

Typically, the intermediate product has a lower concentration of one or more of the C18 fatty acid impurities disclosed above than the feed mixture; and/or the PUFA product produced in the second separation step has a lower concentration of one or more of the C18 fatty acid impurities disclosed above than the intermediate product.

More typically, the intermediate product has a lower concentration of impurities selected from ALA, mono, di- and triglycerides of ALA and $C_1$-$C_4$ alkyl esters of ALA than the feed mixture; and/or the PUFA product produced in the second separation step has a lower concentration of said impurities than the intermediate product.

More typically, the intermediate product has a lower concentration of impurities selected from GLA, mono, di- and triglycerides of GLA and $C_1$-$C_4$ alkyl esters of GLA than the feed mixture; and/or the PUFA product produced in the second separation step has a lower concentration of said impurities than the intermediate product.

Preferably, the intermediate product has a lower concentration of C18 fatty acids or C18 fatty acid derivatives than the feed mixture; or the PUFA product produced in the second separation step has a lower concentration of C18 fatty acids or C18 fatty acid derivatives than the intermediate product. In certain embodiments the intermediate product has a lower concentration of C18 fatty acids or C18 fatty acid derivatives than the feed mixture; and the PUFA product produced in the second separation step has a lower concentration of C18 fatty acids or C18 fatty acid derivatives than the intermediate product.

A lower concentration typically means a concentration which is lower by an amount of 5 wt % or more, more typically 10 wt % or more, preferably 20 wt % or more, more preferably 30 wt % or more, even more preferably 40 wt % or more, yet more preferably 50 wt % or more, yet more preferably 60 wt % or more, yet more preferably 70 wt % or more, yet more preferably 80 wt % or more, yet more preferably 90 wt % or more. Thus, when the intermediate product has a lower concentration of one or more of the C18 fatty acid impurities disclosed above than the feed mixture, the concentration of the C18 fatty acid impurities in the intermediate product is typically 10 wt % or more, preferably 20 wt % or more etc, lower than the concentration of the C18 fatty acid impurities in the feed mixture. When the PUFA product produced in the second separation step has a lower concentration of one or more of the C18 fatty acid impurities disclosed above than the intermediate product, the concentration of the C18 fatty acid impurities in the PUFA product is typically 10 wt % or more, preferably 20 wt % or more etc, lower than the concentration of the C18 fatty acid impurities in the intermediate product.

Typically, the first organic solvent is acetonitrile, and the intermediate product has a lower concentration of one or more of the C18 fatty acid impurities disclosed above than the feed mixture. Alternatively, the second organic solvent is acetonitrile, and the PUFA product produced in the second separation step has a lower concentration of one or more of the C18 fatty acid impurities disclosed above than the intermediate product.

Preferably, the PUFA product is EPA ethyl ester, and (i) the first organic solvent is acetonitrile, and the intermediate product has a lower concentration of one or more of the C18 fatty acid impurities disclosed above than the feed mixture, or (ii) the second organic solvent is acetonitrile, and the PUFA product produced in the second separation step has a lower concentration of one or more of the C18 fatty acid impurities disclosed above than the intermediate product.

More preferably, the PUFA product is EPA ethyl ester, and (i) the first organic solvent is acetonitrile, the second organic solvent is methanol and the intermediate product has a lower concentration of one or more of the C18 fatty acid impurities disclosed above than the feed mixture, or (ii) the first organic solvent is methanol, the second organic solvent is acetonitrile, and the PUFA product produced in the second separation step has a lower concentration of one or more of the C18 fatty acid impurities disclosed above than the intermediate product.

More preferably, the PUFA product is EPA ethyl ester, and (i) the first organic solvent is acetonitrile, the second organic solvent is methanol, and the first chromatographic separation step comprises introducing the feed mixture into a stationary bed apparatus and the second chromatographic separation step comprises introducing the intermediate product into a simulated or actual moving bed chromatography apparatus; or (ii) the first organic solvent is methanol and the second organic solvent is acetonitrile, the first chromatographic separation step comprises introducing the feed mixture into a simulated or actual moving bed chromatography apparatus and the second chromatographic separation step comprises introducing the intermediate product into a stationary bed chromatography apparatus.

Even more preferably, the PUFA product is EPA ethyl ester, and (i) the first organic solvent is acetonitrile, the second organic solvent is methanol, the intermediate product has a lower concentration of one or more of the C18 fatty acid impurities disclosed above than the feed mixture, and the first chromatographic separation step comprises introducing the feed mixture into a stationary bed apparatus and the second chromatographic separation step comprises introducing the intermediate product into a simulated or actual moving bed chromatography apparatus; or (ii) the first organic solvent is methanol, the second organic solvent is acetonitrile, the PUFA product produced in the second separation step has a lower concentration of one or more of the C18 fatty acid impurities disclosed above than the intermediate product, and the first chromatographic separation step comprises introducing the feed mixture into a simulated or actual moving bed chromatography apparatus and the second chromatographic separation step comprises introducing the intermediate product into a stationary bed chromatography apparatus.

The present invention also provides a PUFA product, as defined above, which is obtainable by the process of the present invention.

The present invention also provides a composition comprising a PUFA product of the present invention.

Such compositions typically contain, as PUFA product, EPA or EPA ethyl ester.

The PUFA product is typically present in the compositions in an amount in an amount greater than 90 wt %, preferably greater than 95 wt %, more preferably greater than 97 wt %, even more preferably greater than 98 wt %, still more preferably greater than 98.4 wt %.

Preferably, the PUFA product is EPA or EPA ethyl ester and is present in the compositions in an amount in an amount greater than 90 wt %, preferably greater than 95 wt %, more preferably greater than 97 wt %, even more preferably greater than 98 wt %, still more preferably greater than 98.4 wt %, for example in an amount between 98 and 99.5 wt %.

Typically, the PUFA product contains less than 1 wt % of one or more of the C18 fatty acid impurities disclosed above.

Typically, the PUFA product contains less than 1 wt % of alpha-linolenic acid (ALA), ALA mono-, di- and triglyceride and ALA $C_1$-$C_4$ alkyl ester impurities. More typically, the PUFA product contains less than 1 wt % of impurities which are ALA and derivatives thereof. Typical ALA derivatives are as defined above for PUFA derivatives.

Typically, the PUFA product contains less than 1 wt % of gamma-linolenic acid (GLA), GLA mono-, di- and triglyceride and GLA $C_1$-$C_4$ alkyl ester impurities. More typically, the PUFA product contains less than 1 wt % of impurities which are GLA and derivatives thereof. Typical GLA derivatives are as defined above for PUFA derivatives.

Typically, the PUFA product contains less than 1 wt % of C18 fatty acid impurities, C18 fatty acid mono-, di- and triglyceride and C18 fatty acid alkyl ester impurities. More typically, the PUFA product contains less than 1 wt % of impurities which are C18 fatty acids and derivatives thereof. For the avoidance of doubt, in this embodiment the maximum amount of all such impurities is 1 wt %. Typical C18 fatty acid derivatives are as defined above for PUFA derivatives. As used herein, a C18 fatty acid is a C18 aliphatic monocarboxylic acid having a straight or branched hydrocarbon chain. Typical C18 fatty acids include stearic acid (C18:0), oleic acid (C18:1n9), vaccenic acid (C18:1n7), linoleic acid (C18:2n6), gamma-linolenic acid/GLA (C18:3n6), alpha-linolenic acid/ALA (C18:3n3) and stearidonic acid/SDA (C18:4n3).

As explained above, typically the amount of the above-mentioned impurities in the PUFA product is less than 1 wt %. Preferably, the amount of the above-mentioned impurities is less than 0.5 wt %, more preferably less than 0.25 wt %, even more preferably less than 0.1 wt %, yet more preferably less than 0.05 wt %, yet more preferably less than 0.01 wt %, yet more preferably less than 0.001 wt %, yet more preferably less than 0.0001 wt %, yet more preferably less than 0.00001 wt %.

In certain preferred embodiments, the PUFA product is substantially free of the above-mentioned impurities.

The PUFA product is not ALA, GLA, linoleic acid, an ALA mono- di- or triglyceride, a GLA mono- di- or triglyceride, an oleic acid mono-, di- or triglyceride, an ALA $C_1$-$C_4$ alkyl ester, a GLA $C_1$-$C_4$ alkyl ester or an oleic acid $C_1$-$C_4$ alkyl ester or a mixture thereof. Typically, the PUFA product is not ALA, GLA, linoleic acid, or a derivative or mixtures thereof. Typical ALA, GLA and linoleic acid derivatives are as defined above for PUFA derivatives.

Typically, the PUFA product is not a C18 PUFA, a C18 PUFA mono-, di-or triglyceride, or a C18 PUFA alkyl ester. More typically, the PUFA product is not a C18 PUFA or a C18 PUFA derivative. Typical C18 PUFAs include linoleic acid (C18:2n6), GLA (C18:3n6), and ALA (C18:3n3).

Typically, the composition comprises, as PUFA product, EPA or EPA ethyl ester present in an amount between 98 and 99.5 wt %, the composition containing less than 1 wt % of ALA ethyl ester.

Typically, the composition comprises, as PUFA product, EPA or EPA ethyl ester present in an amount between 98 and 99.5 wt %, the composition containing less than 1 wt % of GLA ethyl ester.

Preferably, the composition comprises, as PUFA product, EPA or EPA ethyl ester present in an amount between 98 and 99.5 wt %, the composition containing less than 1 wt % of ALA, ALA mono-, di- and triglycerides and ALA $C_1$-$C_4$ alkyl esters.

Preferably, the composition comprises, as PUFA product, EPA or EPA ethyl ester present in an amount between 98 and 99.5 wt %, the composition containing less than 1 wt % of GLA, GLA mono-, di- or triglycerides and GLA $C_1$-$C_4$ alkyl esters.

More preferably, the composition comprises, as PUFA product, EPA ethyl ester present in an amount between 98 and 99.5 wt %, the composition containing less than 1 wt % of ALA, ALA mono-, di- or triglycerides and ALA $C_1$-$C_4$ alkyl esters.

More preferably, the composition comprises, as PUFA product, EPA ethyl ester present in an amount between 98 and 99.5 wt %, the composition containing less than 1 wt % of GLA, GLA mono-, di- or triglycerides and GLA $C_1$-$C_4$ alkyl esters.

The following Examples illustrate the invention.

EXAMPLES

Example 1

First Chromatographic Separation Step

Figure 16:
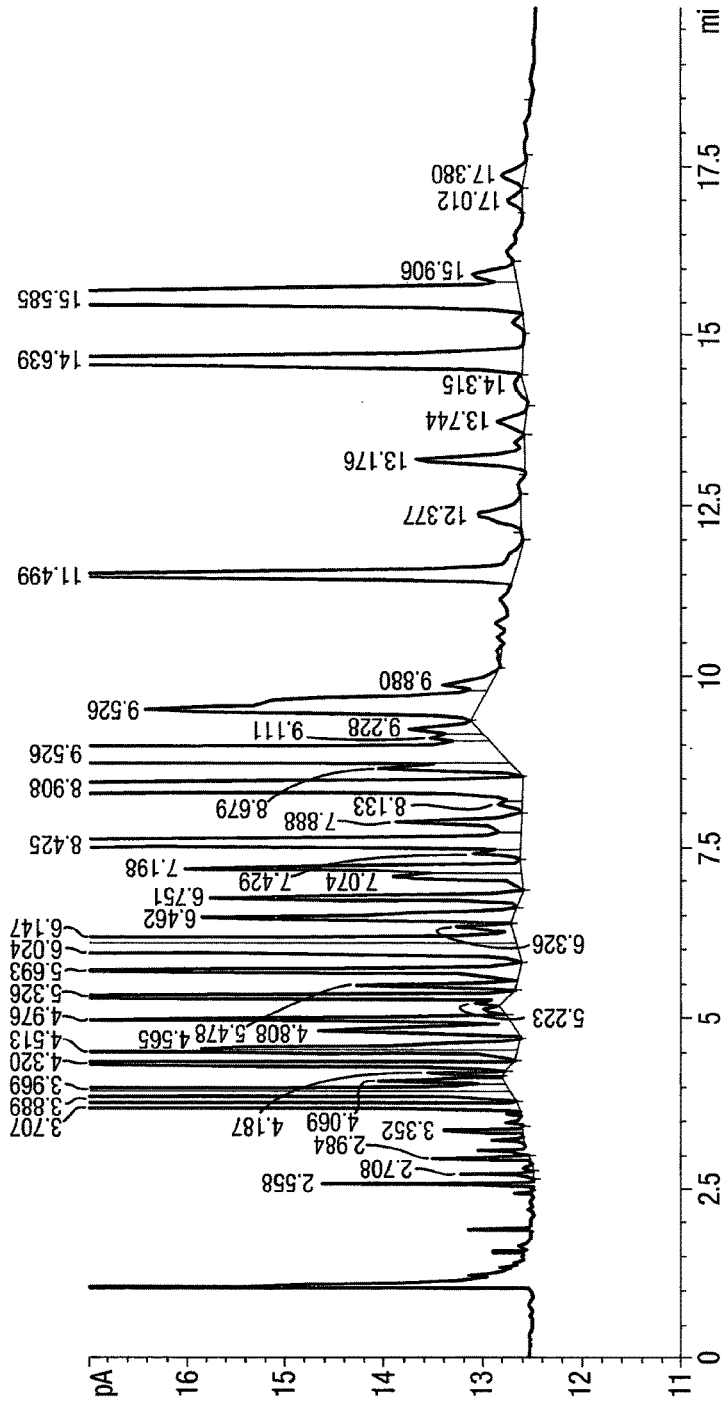
FIG. 16 shows a GC-FAMES trace of a typical feed mixture, which contains 55% wt % EPA ethyl ester.

A fish oil derived feedstock (55weight % EPA ethyl ester (EE), 5 weight % DHA EE) with fatty acid profile as shown in FIG. 16 was fractionated using an actual moving bed chromatography system using bonded C18 silica gel (particle size 300 µm, particle porosity 150 angstroms) as stationary phase and aqueous methanol (typically 0.5% to 10% water) as eluent through a "single pass" SMB apparatus consisting of 15 columns (diameter: 76.29 mm, length: 914.40 mm) connected in series.

Figure 12:
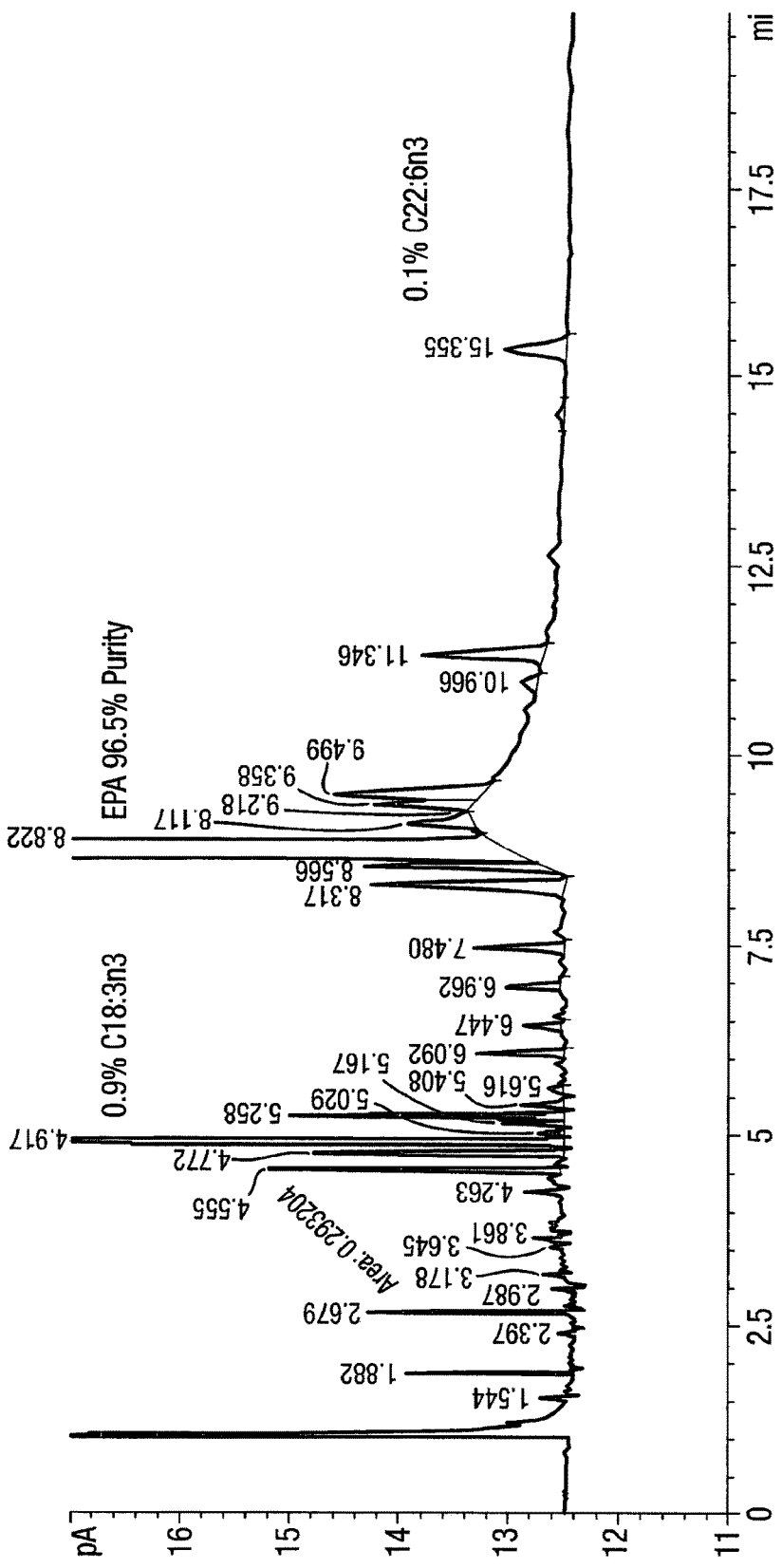
FIG. 12 shows a GC-FAMES trace of an intermediate product produced by the first separation step of the process of the present invention where methanol is used as first organic solvent.

The operating parameters and flowrates are as follows. (typical flow scheme as per FIG. 8)
Step time: 750 secs
Cycle time: 200 mins
Feed mixture feed rate (F1): 74 ml/min
Desorbent feed rate (D1): 6250 ml/min
Extract accumulation rate (E1): 1250 ml/min
Extract recycle rate (D1-E1): 5000 ml/min
Raffinate accumulation rate (R1): 1688 ml/min
Cycle time: 600 secs The intermediate product produced by this process has a GC-FAMES trace as shown in FIG. 12. EPA EE is contained at 96.5% purity. The major impurity is ethyl-alpha linolenoate (ALA—C18:3n3) present at 0.9%. ALA is present in the raw material at 0.65%. ALA can therefore be seen to co-elute with EPA using methanol/water as the mobile phase. Methanol/water is, however, very efficient at removing the closely related component ethyl-docosahexaenoate (DHA—C22:6n3).

Second Chromatographic Separation Step

The intermediate product produced in the first chromatographic separation step was further purified by preparative HPLC in a fixed bed using an acetonitrile/water mobile phase mix. Acetonitrile/water in a ratio of 87:13 by wt was utilised. An HPLC column of dimensions 600 mm×900 mm packed with c18 bonded silica (20 µm particle size) is used with a feed mixture injection volume of 1400 ml and a desorbent flow rate of 2200 ml/min.

Figure 13:
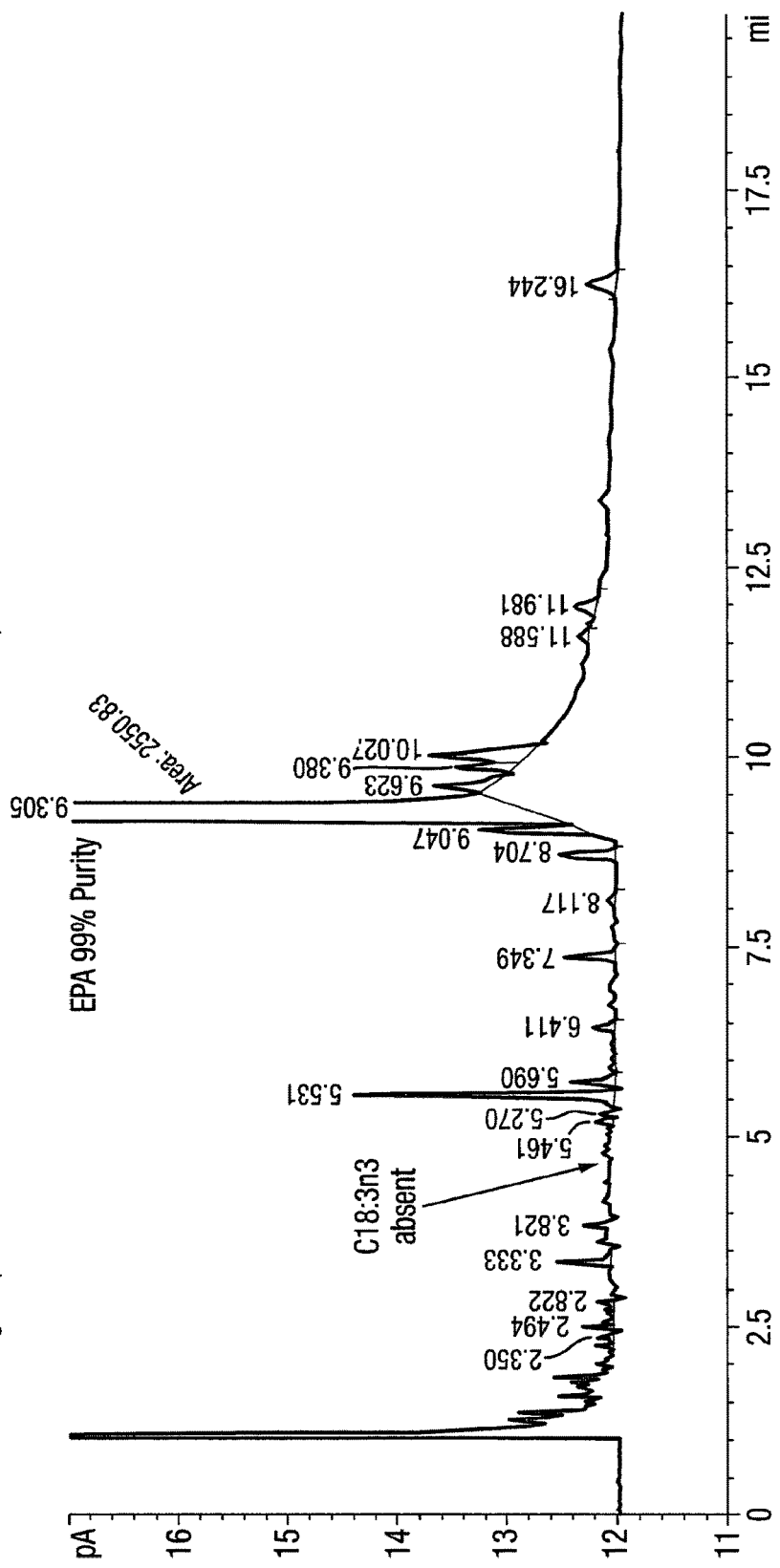
FIG. 13 shows a GC-FAMES trace of a PUFA product produced by the second separation step of the process of the present invention where acetonitrile is used as second organic solvent.

The final PUFA product produced was analysed by GC FAMES and the trace is shown in FIG. 13. It can be see that ALA has been completely removed and the EPA purity increased to 98.5%.

Alternative Second Chromatographic Separation Step

The intermediate product produced in the first chromatographic separation step was fractionated using an actual moving bed chromatography system using bonded C18 silica gel (particle size 300 µm, particle porosity 150 angstroms) as stationary phase and aqueous acetonitrile (12% water) as eluent through a "single pass" SMB apparatus consisting of 8 columns (diameter: 76.29 mm, length: 914.40 mm) connected in series.

The operating parameters and flowrates are as follows. (typical flow scheme as per FIG. 8)
Step time: 780 secs
Feed mixture feed rate (F1): 90 ml/min
Desorbent feed rate (D1): 6500 ml/min
Extract accumulation rate (E1): 1400 ml/min
Extract recycle rate (D1-E1): 5100 ml/min
Raffinate accumulation rate (R1): 1690 ml/min
Cycle time: 600 secs

Example 2

First Chromatographic Separation Step

Figure 14:
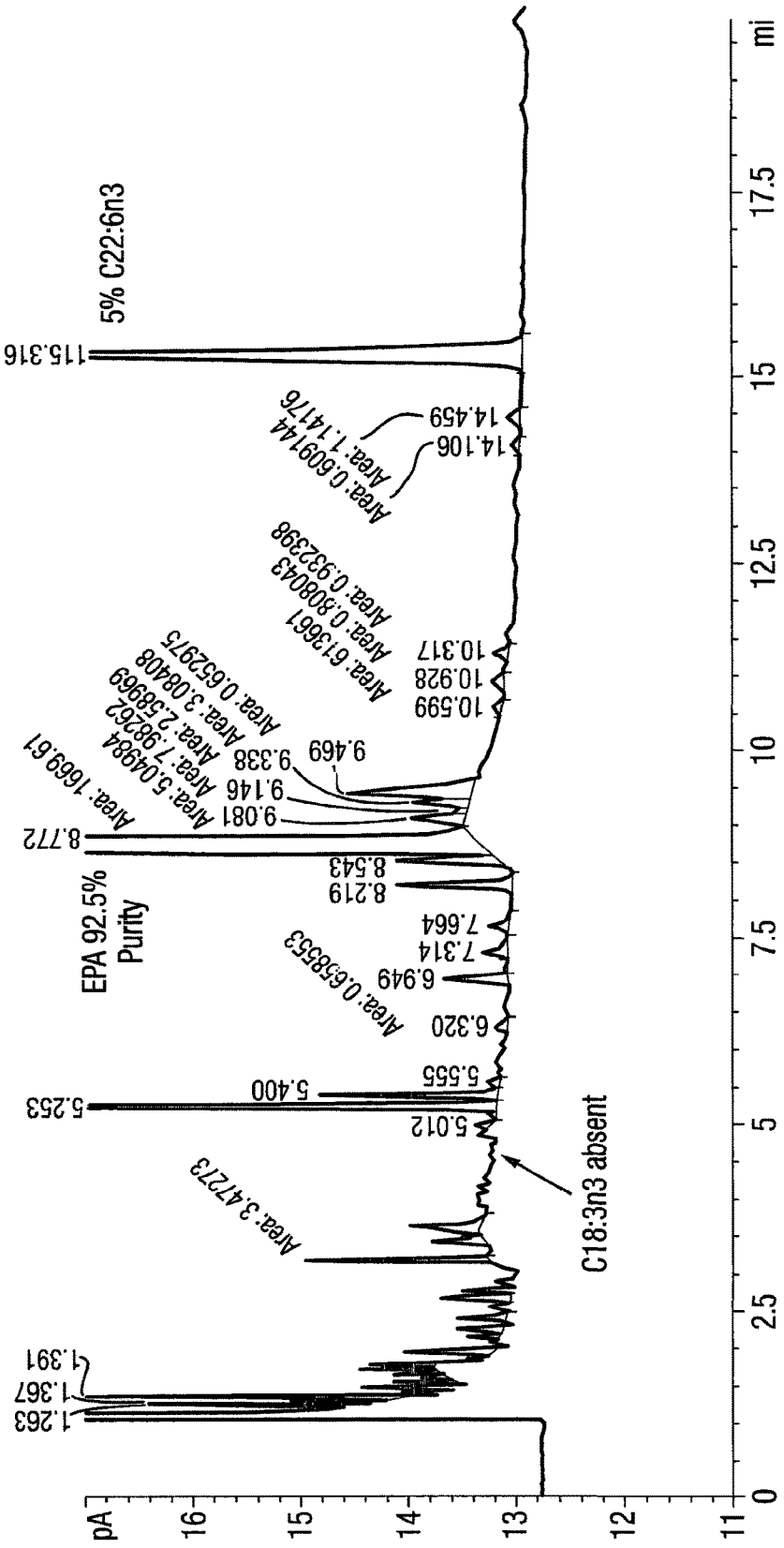
FIG. 14 shows a GC-FAMES trace of an intermediate product produced by the first separation step of the process of the present invention where acetonitrile is used as first organic solvent.

A fish oil derived feedstock (55weight % EPA EE, 5 weight % DHA EE) with fatty acid profile as shown in FIG. 16 was subjected to preparative HPLC separation using an acetonitrile/water eluent. The mobile phase used is 87:13 Acetonitrile:water. An HPLC column of dimensions 600 mm×900 mm packed with c18 bonded silica (20 µm particle size) is used with a feed mixture injection volume of 600 ml and a desorbent flow rate of 2200 ml/min. The intermediate product produced was analysed by GC FAME and the trace is shown as FIG. 14.

It can be seen that ethyl-alpha-linolenoate (ALA—C18: 3n3) was completely removed from the feed mixture. However a purity level of only 92.5% EPA EE was achieved mainly due to the presence of a high level of ethyl-docosahexaenoate (DHA—C22:6n3).

Alternative First Chromatographic Separation Step

A fish oil derived feedstock (55 weight % EPA EE, 5 weight % DHA EE) with fatty acid profile as shown in FIG. 16 was fractionated using an actual moving bed chromatography system using bonded C18 silica gel (particle size 300 µm, particle porosity 150 angstroms) as stationary phase and aqueous acetonitrile (typically 4% to 18% water) as eluent through a "single pass" SMB apparatus consisting of 15 columns (diameter: 76.29 mm, length: 914.40 mm) connected in series.

The operating parameters and flowrates are as follows. (typical flow scheme as per FIG. 8)
Step time: 600 secs
Feedstock (F) feed rate: 105 ml/min
Desorbent (D) feed rate: 4800 ml/min
Extract rate: 1250 ml/min
Raffinate rate: 1800 ml/min Second Chromatographic Separation Step The intermediate product produced was subjected to further purification using preparative HPLC using as eluent methanol/water at 88:12 ratio by wt. An HPLC column of dimensions 600 mm×900 mm packed with c18 bonded silica (20 µm particle size) is used with a feed mixture injection volume of 1250 ml and a desorbent flow rate of 2200 ml/min.

Figure 15:
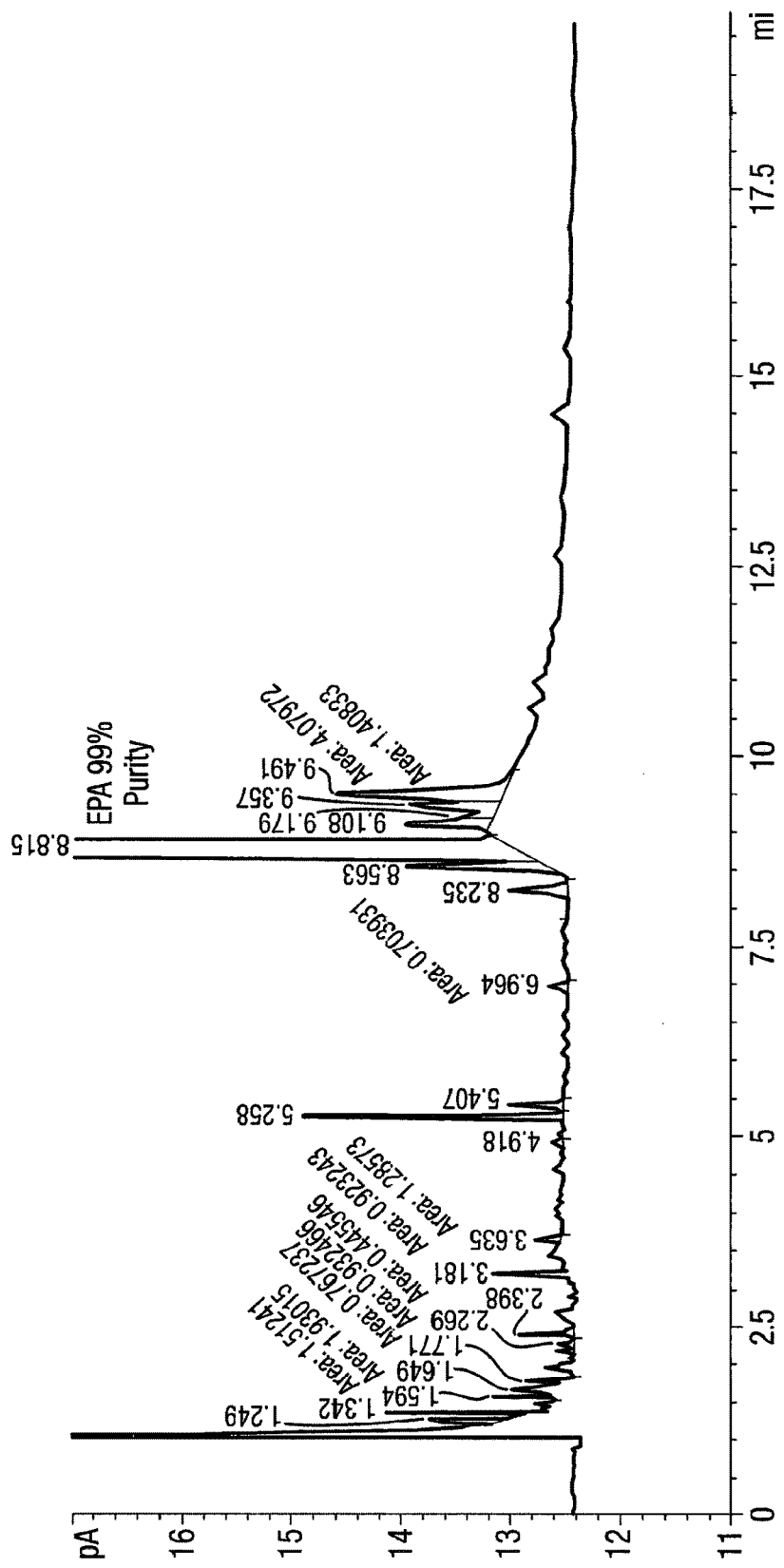
FIG. 15 shows a GC-FAMES trace of a PUFA product produced by the second separation step of the process of the present invention where methanol is used as second organic solvent.

The final product produced has a GC FAMES trace as shown in FIG. 15. The product produced contains EPA EE at 99% purity.

Thus, it can be seen that the outcome from performing acetonitrile/water separation first followed by methanol/water is essentially the same as performing methanol/water first followed by acetonitrile/water. In each case combining a step involving methanol/water and a further step involving acetonitrile/water is advantageous in preparing a highly purified EPA (EE) concentrate at .about.99% purity with a low content of C18 fatty acid impurities, for example ALA.

Alternative Second Chromatographic Separation Step

The intermediate product produced was fractionated using an actual moving bed chromatography system using bonded C18 silica gel (particle size 300 µm, particle porosity 150 angstroms) as stationary phase and aqueous methanol (7% water) as eluent through a "single pass" SMB consisting of 8 columns (diameter: 76.29 mm, length: 914.40 mm) connected in series.

The operating parameters and flowrates are as follows. (typical flow scheme as per FIG. 8)
Step time: 960 secs
Feedstock (F) feed rate: 45 ml/min
Desorbent (D) feed rate: 3975 ml/min
Extract rate: 3655 ml/min
Raffinate rate: 2395 ml/min Comparative Example 1

A fish oil derived feedstock (55 weight % EPA EE, 5 weight % DHA EE) with fatty acid profile as shown in FIG. 16 is fractionated in first and second chromatographic separation steps using an actual moving bed chromatography system using bonded C18 silica gel (particle size 300 μm, particle porosity 150 angstroms) as stationary phase and aqueous methanol as eluent in both separation steps.

First separation step performed on a series of 8 columns (diameter: 76.29 mm, length: 914.40 mm) connected in series.

The operating parameters and flowrates are as follows. (typical flow scheme as per FIG. 8)
Feed mixture feed rate (F1): 34 ml/min
Desorbent feed rate (D1): 14438 ml/min
Extract accumulation rate (E1): 9313 ml/min
Extract recycle rate (D1-E1): 5125 ml/min
Raffinate accumulation rate (R1): 1688 ml/min
Cycle time: 1200 secs Second separation step performed on a second series of 7 columns (diameter: 76.29 mm, length: 914.40 mm) connected in series.

Second intermediate product feed rate (F3): 40 ml/min
Desorbent feed rate (D3): 6189 ml/min
Extract accumulation rate (E3): 1438 ml/min
Extract recycle rate (D3-E3): 4750 ml/min
Raffinate accumulation rate (R3): 1438 ml/min
Cycle time: 1080 secs The comparative example produced an EPA concentrate with a less advantageous impurity profile. The upper purity achievable is limited in particular by the presence of C18:3 components (GLA and ALA).

What is claimed is:

1. A composition comprising a PUFA product, wherein the PUFA product comprises C18 fatty acid impurities, and wherein the amount of the C18 fatty acid impurities in the PUFA product is up to 0.25 wt %.

2. The composition according to claim 1, wherein the PUFA product contains an amount of C18 fatty acid impurities, C18 fatty acid mono-, di- and triglyceride and C18 fatty acid alkyl ester impurities up to 0.25 wt %.

3. The composition according to claim 1, wherein the PUFA product is at least one ω-3 PUFA or a PUFA derivative.

4. The composition according to claim 3, wherein the PUFA derivative is a PUFA in the form of a mono-, di- or triglyceride, ester, phospholipid, amide, lactone, or salt.

5. The composition according to claim 1, wherein the PUFA product is other than a C18 PUFA, a C18 PUFA mono-, di- or triglyceride, or a C18 PUFA alkyl ester.

6. The composition according to claim 1, wherein the PUFA product is present in the composition in an amount greater than 90 wt %.

7. The composition according to claim 6, wherein the PUFA product is present in the composition in an amount greater than 95 wt % or greater than 97 wt % or greater than 98 wt %.

8. The composition according to claim 1, wherein the PUFA product is EPA or EPA ethyl ester.

9. The composition according to claim 1, wherein the PUFA product is EPA or EPA ethyl ester and is present in the compositions in an amount greater than 90 wt %.

10. The composition according to claim 9, wherein the PUFA product is EPA or EPA ethyl ester and is present in the compositions in an amount greater than 95 wt % or greater than 97 wt % or greater than 98 wt %.

11. The composition according to claim 1, wherein the PUFA product is EPA or EPA ethyl ester and is present in the compositions in an amount between 98 and 99.5 wt %.

\* \* \* \* \*